(12) United States Patent
Xue et al.

(10) Patent No.: US 12,031,160 B2
(45) Date of Patent: Jul. 9, 2024

(54) METHOD FOR THE PRODUCTION OF GLUFOSINATE-AMMONIUM

(71) Applicant: ZHEJIANG UNIVERSITY OF TECHNOLOGY, Zhejiang (CN)

(72) Inventors: Yaping Xue, Zhejiang (CN); Feng Cheng, Zhejiang (CN); Qinghua Li, Zhejiang (CN); Yuguo Zheng, Zhejiang (CN); Jianmiao Xu, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 341 days.

(21) Appl. No.: 17/419,048

(22) PCT Filed: Jun. 28, 2019

(86) PCT No.: PCT/CN2019/093462
§ 371 (c)(1),
(2) Date: Jun. 28, 2021

(87) PCT Pub. No.: WO2020/133990
PCT Pub. Date: Jul. 2, 2020

(65) Prior Publication Data
US 2022/0090029 A1 Mar. 24, 2022

(30) Foreign Application Priority Data
Dec. 28, 2018 (CN) .......................... 201811621710.0

(51) Int. Cl.
*C12P 13/04* (2006.01)
*C12N 9/06* (2006.01)

(52) U.S. Cl.
CPC ............ *C12N 9/0016* (2013.01); *C12P 13/04* (2013.01)

(58) Field of Classification Search
CPC ...... C12N 9/0016; C12P 13/04; C12Y 104/01
See application file for complete search history.

(56) References Cited

FOREIGN PATENT DOCUMENTS

| CN | 107502647 A | 12/2017 |
| CN | 108588045 A | 9/2018 |
| CN | 109609475 A | 4/2019 |

OTHER PUBLICATIONS

Hanson et al., Bioorganic & Medicinal Chemistry 7:2247-2252, 1999.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
NADP-Specific Glutamate Dehydrogenase [Pseudomonas Moorei]; Aug. 6, 2017; 1 page; NCBI WP_090325311.1.

* cited by examiner

*Primary Examiner* — Delia M Ramirez
(74) *Attorney, Agent, or Firm* — Muncy, Geissler, Olds & Lowe, P.C.

(57) ABSTRACT

The present invention provides a glufosinate-ammonium dehydrogenase mutant and application in synthesis of L-glufosinate-ammonium thereof, the method uses 2-carbonyl-4-[(hydroxy)(methyl)phosphinoyl]-butyric acid or its salts as a substrate and the glufosinate-ammonium dehydrogenase or cells containing the glufosinate-ammonium dehydrogenase as a biocatalyst to carry out reductive amination, thereby obtaining L-glufosinate-ammonium. The method has features of high conversion rate of raw materials, high yield, easy separation and purification of the product, and high chiral purity; compared with other catalytic processes, the method in the present invention has features of relatively simple process and a conversion rate of raw materials up to 100%.

5 Claims, 5 Drawing Sheets
Specification includes a Sequence Listing.

SEQUENCE LISTING

<160> NUMBER OF SEQ ID NOS: 10

<210> SEQ ID NO 1
<211> LENGTH: 1338
<212> TYPE: DNA
<213> ORGANISM: Pseudomonas

<400> SEQUENCE: 1

```
atgatcgaat ccgtggaatc attcttagct cgcctgaaga agcgcgatcc cgaccaacca      60
gaatttcatc aagctgtcga ggaagtgctt cgtagcctgt ggccttttt agaggccaac     120
ccgcactatc tggcatcggg gatttagaa cgcatttgcg aaccggaacg cgcaattact     180
tttcgcgttt catgggtaga cgatcatggc aaggtgcaag ttaatcgtgg gtttcgcatc     240
caaatgaata gcgcaatcgg accatacaaa gggggacttc gttttcatcc ttctgtaaat     300
ttaggggtac tgaaattttt ggcgttcgag cagacgttca agaattcact gacgtctctt     360
ccgatgggtg gcgtaaagg cgggagcgac tttgatccga aggcaagtc cgacgcagaa      420
gtgatgcgtt tttgccaggc tttatgtcc gagctgtatc gccatattgg agctgacgtg     480
gatgtcccgg ccgtgatat tggcgttggc gcacgcgaga ttggatttt atttggccaa      540
tataagcgtc tgtctaacca gtttacatcc gtgctgacag aaaaggtat gacgtacggc     600
ggctctctta tccgccctga agctacgggc ttcggttgtg tgtactttgc agaggagatg    660
cttaaacgcg atgggcaacg tgtagagggt aagcgcgtgg ctgtcagtgg gagcgggaac    720
gtagcccaat acgccgcacg caaggtgatg gaccttggag ggaaagtgat tagtctttcc    780
gacagtgagg ggaccttgta tgctgaaagc ggtttgaccg aggaacaatg gtcagcgctg    840
ttagagctta agaatgtgca acgcgggcgt atttcggaac ttgcaggccg ctacggactt    900
gaatttcgcg ctggcaaaac tccgtgggag cttgcttgtg acatcgcttt gccttgcgcg    960
acacagaatg agcttgacgc cgaagcggct cgcacgttgt tacgtaatgg atgtatttgt   1020
gttgcagaag gtgctaacat gccaacgact ttagaggctg ttgacattt tatcgaagcg    1080
gggatccttt tcgccccagg caaagctagt aacgctgggg gtgtagcggt ctctggttg    1140
gaaatgtctc agaatgccat gcgcttattg tggaccgcag gtgaggtcga ctctaagtta   1200
cacaatatca tgcaaagtat ccatcacgca tgtgtacact acggggaaga gaatggccgc   1260
atcaactacg tgaaaggcgc gaatatcgcg ggattcgtaa aggtcgcaga cgctatgctt   1320
gcccagggaa tcgtgtaa                                                  1338
```

<210> SEQ ID NO 2
<211> LENGTH: 445
<212> TYPE: PRT
<213> ORGANISM: Pseudomonas

<400> SEQUENCE: 2

```
Met Ile Glu Ser Val Glu Ser Phe Leu Ala Arg Leu Lys Lys Arg Asp
1               5                   10                  15

Pro Asp Gln Pro Glu Phe His Gln Ala Val Glu Glu Val Leu Arg Ser
            20                  25                  30

Leu Trp Pro Phe Leu Glu Ala Asn Pro His Tyr Leu Ala Ser Gly Ile
        35                  40                  45

Leu Glu Arg Ile Cys Glu Pro Glu Arg Ala Ile Thr Phe Arg Val Ser
    50                  55                  60

Trp Val Asp Asp His Gly Lys Val Gln Val Asn Arg Gly Phe Arg Ile
65                  70                  75                  80
```

```
Gln Met Asn Ser Ala Ile Gly Pro Tyr Lys Gly Gly Leu Arg Phe His
                 85                  90                  95

Pro Ser Val Asn Leu Gly Val Leu Lys Phe Leu Ala Phe Glu Gln Thr
            100                 105                 110

Phe Lys Asn Ser Leu Thr Ser Leu Pro Met Gly Gly Lys Gly
            115                 120                 125

Ser Asp Phe Asp Pro Lys Gly Lys Ser Asp Ala Glu Val Met Arg Phe
130                 135                 140

Cys Gln Ala Phe Met Ser Glu Leu Tyr Arg His Ile Gly Ala Asp Val
145                 150                 155                 160

Asp Val Pro Ala Gly Asp Ile Gly Val Gly Ala Arg Glu Ile Gly Phe
                165                 170                 175

Leu Phe Gly Gln Tyr Lys Arg Leu Ser Asn Gln Phe Thr Ser Val Leu
                180                 185                 190

Thr Gly Lys Gly Met Thr Tyr Gly Gly Ser Leu Ile Arg Pro Glu Ala
                195                 200                 205

Thr Gly Phe Gly Cys Val Tyr Phe Ala Glu Glu Met Leu Lys Arg Asp
            210                 215                 220

Gly Gln Arg Val Glu Gly Lys Arg Val Ala Val Ser Gly Ser Gly Asn
225                 230                 235                 240

Val Ala Gln Tyr Ala Ala Arg Lys Val Met Asp Leu Gly Gly Lys Val
                245                 250                 255

Ile Ser Leu Ser Asp Ser Glu Gly Thr Leu Tyr Ala Glu Ser Gly Leu
                260                 265                 270

Thr Glu Glu Gln Trp Ser Ala Leu Leu Glu Leu Lys Asn Val Gln Arg
                275                 280                 285

Gly Arg Ile Ser Glu Leu Ala Gly Arg Tyr Gly Leu Glu Phe Arg Ala
                290                 295                 300

Gly Lys Thr Pro Trp Glu Leu Ala Cys Asp Ile Ala Leu Pro Cys Ala
305                 310                 315                 320

Thr Gln Asn Glu Leu Asp Ala Glu Ala Arg Thr Leu Leu Arg Asn
                325                 330                 335

Gly Cys Ile Cys Val Ala Glu Gly Ala Asn Met Pro Thr Thr Leu Glu
            340                 345                 350

Ala Val Asp Ile Phe Ile Glu Ala Gly Ile Leu Phe Ala Pro Gly Lys
            355                 360                 365

Ala Ser Asn Ala Gly Gly Val Ala Val Ser Gly Leu Glu Met Ser Gln
            370                 375                 380

Asn Ala Met Arg Leu Leu Trp Thr Ala Gly Glu Val Asp Ser Lys Leu
385                 390                 395                 400

His Asn Ile Met Gln Ser Ile His His Ala Cys Val His Tyr Gly Glu
                405                 410                 415

Glu Asn Gly Arg Ile Asn Tyr Val Lys Gly Ala Asn Ile Ala Gly Phe
                420                 425                 430

Val Lys Val Ala Asp Ala Met Leu Ala Gln Gly Ile Val
                435                 440                 445

<210> SEQ ID NO 3
<211> LENGTH: 1338
<212> TYPE: DNA
<213> ORGANISM: Pseudomonas extremaustralis

<400> SEQUENCE: 3
atgatcgaat ctgtcgaaag tttcctggcg cgtttgaaga agcgtgaccc agatcaaccc      60
```

```
gagtttcatc aggctgtgga agaagtttta cgcagcttat ggcccttcct tgaagcaaat    120
cctcactatt taacatcggg tatcctggaa cgtatctgtg agccagagcg cgctatcatt    180
ttccgcgtca gttgggttga tgaccacggg aaggtgcaag tgaaccgcgg tttccgtatc    240
caaatgaact cggctatcgg tccttacaaa ggaggcttgc gctttcatcc ctcagtaaac    300
ctgggtgtat taaaatttct tgctttcgaa cagacatttt aaaattccct gacctccttg    360
ccgatgggtg gggcaaggg aggtagcgat tttgacccaa aaggaaaatc tgacgcggaa    420
gtaatgcgtt tttgtcaagc atttatgagc gagctttacc gccatattgg cgcggatgtg    480
gacgtcccag cgggcgatat tggcgtcggt gcccgcgaaa tcgggttcct gtttggccag    540
tataaacgcc tttcaaacca gtttacctca gtgttgactg ggaagggtat gacttatggt    600
ggaagtttga ttcgtccaga ggctacgggt ttcgggtgcg tctatttgc cgaggagatg    660 ctgaagcgcg atgatcaacg tgtggagggt aagcgcgtgg caatcagtgg gtccggcaat    720
gtcgcccagt acgcagcgcg taaggtaatg gaccttgggg aaaagtaat ctcgcttagc    780 gatagtgagg ggacgttata cgccgagtca ggtttaactg aagctcaatg gtcggcactg    840
ctggagctga agaatgtaca acgtggacgt attagtgaac tggcacagcg ctttggtctg    900
gaatttcgca aagggaaaac gccatgggag ttagcgtgtg acatcgcctt accgtgcgcc    960
acacagaatg agttagacgc ccaagcagct cgcacgcttt tgcacaatgg atgtatctgc    1020
gtcgctgagg gggccaatat gcctaccacc ttggaagcag tagatatctt tattgaagct    1080
ggcatcctgt tcgcccccgg taaggcttcc aatgcaggtg gcgtagcggt tctggtttta    1140
gagatgtcac agaacgctat gcgcttgctt tggacggctg gcgaagtaga cagcaagttg    1200
cacaacatta tgcagtcgat ccaccatgcg tgcgtccact acggggaaga aaatgggcgc    1260
gtgaactatg tgaaaggtgc taacattgct ggtttcgtga aggtagctga cgcgatgctt    1320
gctcagggca ttgtataa                                                  1338
```

<210> SEQ ID NO 4
<211> LENGTH: 445
<212> TYPE: PRT
<213> ORGANISM: Pseudomonas extremaustralis

<400> SEQUENCE: 4

```
Met Ile Glu Ser Val Glu Ser Phe Leu Ala Arg Leu Lys Lys Arg Asp
1               5                   10                  15

Pro Asp Gln Pro Glu Phe His Gln Ala Val Glu Glu Val Leu Arg Ser
            20                  25                  30

Leu Trp Pro Phe Leu Glu Ala Asn Pro His Tyr Leu Thr Ser Gly Ile
        35                  40                  45

Leu Glu Arg Ile Cys Glu Pro Glu Arg Ala Ile Ile Phe Arg Val Ser
    50                  55                  60

Trp Val Asp Asp His Gly Lys Val Gln Val Asn Arg Gly Phe Arg Ile
65                  70                  75                  80

Gln Met Asn Ser Ala Ile Gly Pro Tyr Lys Gly Leu Arg Phe His
                85                  90                  95

Pro Ser Val Asn Leu Gly Val Leu Lys Phe Leu Ala Phe Glu Gln Thr
            100                 105                 110

Phe Lys Asn Ser Leu Thr Ser Leu Pro Met Gly Gly Lys Gly Gly
        115                 120                 125

Ser Asp Phe Asp Pro Lys Gly Lys Ser Asp Ala Glu Val Met Arg Phe
    130                 135                 140
```

-continued

Cys Gln Ala Phe Met Ser Glu Leu Tyr Arg His Ile Gly Ala Asp Val
145                 150                 155                 160

Asp Val Pro Ala Gly Asp Ile Gly Val Gly Ala Arg Glu Ile Gly Phe
            165                 170                 175

Leu Phe Gly Gln Tyr Lys Arg Leu Ser Asn Gln Phe Thr Ser Val Leu
        180                 185                 190

Thr Gly Lys Gly Met Thr Tyr Gly Gly Ser Leu Ile Arg Pro Glu Ala
    195                 200                 205

Thr Gly Phe Gly Cys Val Tyr Phe Ala Glu Glu Met Leu Lys Arg Asp
    210                 215                 220

Asp Gln Arg Val Glu Gly Lys Arg Val Ala Ile Ser Gly Ser Gly Asn
225                 230                 235                 240

Val Ala Gln Tyr Ala Ala Arg Lys Val Met Asp Leu Gly Gly Lys Val
            245                 250                 255

Ile Ser Leu Ser Asp Ser Glu Gly Thr Leu Tyr Ala Glu Ser Gly Leu
        260                 265                 270

Thr Glu Ala Gln Trp Ser Ala Leu Leu Glu Leu Lys Asn Val Gln Arg
    275                 280                 285

Gly Arg Ile Ser Glu Leu Ala Gln Arg Phe Gly Leu Glu Phe Arg Lys
    290                 295                 300

Gly Lys Thr Pro Trp Glu Leu Ala Cys Asp Ile Ala Leu Pro Cys Ala
305                 310                 315                 320

Thr Gln Asn Glu Leu Asp Ala Gln Ala Arg Thr Leu Leu His Asn
            325                 330                 335

Gly Cys Ile Cys Val Ala Glu Gly Ala Asn Met Pro Thr Thr Leu Glu
        340                 345                 350

Ala Val Asp Ile Phe Ile Glu Ala Gly Ile Leu Phe Ala Pro Gly Lys
    355                 360                 365

Ala Ser Asn Ala Gly Gly Val Ala Val Ser Gly Leu Glu Met Ser Gln
    370                 375                 380

Asn Ala Met Arg Leu Leu Trp Thr Ala Gly Glu Val Asp Ser Lys Leu
385                 390                 395                 400

His Asn Ile Met Gln Ser Ile His His Ala Cys Val His Tyr Gly Glu
            405                 410                 415

Glu Asn Gly Arg Val Asn Tyr Val Lys Gly Ala Asn Ile Ala Gly Phe
        420                 425                 430

Val Lys Val Ala Asp Ala Met Leu Ala Gln Gly Ile Val
    435                 440                 445

<210> SEQ ID NO 5
<211> LENGTH: 1338
<212> TYPE: DNA
<213> ORGANISM: Pseudomonas moorei

<400> SEQUENCE: 5
atgattgaga gcgtcgagtc tttcttggcc cgccttaaaa agcgcgaccc tgaccagccg      60
gagtttcatc aggcagttga ggaagtctta cgctcattat ggccgttcct ggaagctaac     120
ccccgttatt tgactagcgg cattcttgaa cgtatttgcg agccggaacg tgccatcgtt     180
ttccgtgtga gctgggtaga cgaccaagga aaggtgcaag tgaaccgtgg cttccgcatc     240
cagatgaact cagctatcgg cccatataaa ggcgggttgc gttttcatcc aagcgttaat     300
ttgggtgtct taaaattctt agcgttcgag caaacatttt aaaacagctt aacatcgtta     360
cccatgggtg gaggaaaggg tggtagtgac ttcgacccaa aggggaagag cgatgcggaa     420

-continued

```
gtcatgcgtt tctgccaggc attcatgtca gagctttacc gtcacatcgg ggcggacgtc    480
gatgtgccag cgggagatat tggcgtgggt gcgcgcgaga ttggattttt attcggtcag    540
tataagcgtc tgtctaacca gttcacctcg gtacttacgg gtaagggacc gtcatatggc    600
ggcagtttga ttcgcccaga agctaccgga tttggttgtg tttattttgc cgaagaaatg    660
cttaagcgcc gtggagaaac cgtggaaggc aagcgtgttg ccattagtgg ctctgggaac    720
gtagcgcagt atgcggcccg caaggtgatg gatcttggcg gaaaagtcat ttctttatca    780
gacagcgagg gcacattata ctgcgaatcc ggtttgactg aagctcaatg gcaagcagtg    840
ttggaactga agaatgtaca acgtggccgt atttcagaat tagccggacg ctttggtctt    900 gaattttag cgggccaacg ccctgggt ttatcttgcg atatcgccct tccttgcgcg    960
acgcagaacg agcttgacgc cgaagctgcg cgtgctttac ttcgtaatgg atgcacgtgc   1020
gtcgctgaag gggcgaacat gccgacaacc cttgaggcgg ttgatctgtt tatcgaagcg   1080
ggtattctgt tcgctccagg taaagcctcg aatgctggcg gggttgcagt gtcgggttta   1140
gagatgtcgc aaaacgcaat gcgtttattg tggacagggg gcgaggttga ctcaaaattg   1200
catgctatca tgcagagcat ccatcatgct tgcgtacatt acggtgaaga gaacggtcag   1260
gtaaactacg taaggggggc gaatattgct ggattcgtga aggttgctga tgcaatgctg   1320
gcacaggggg tcgtctaa                                                 1338
```

<210> SEQ ID NO 6
<211> LENGTH: 445
<212> TYPE: PRT
<213> ORGANISM: Pseudomonas moorei

<400> SEQUENCE: 6

```
Met Ile Glu Ser Val Glu Ser Phe Leu Ala Arg Leu Lys Lys Arg Asp
1               5                   10                  15

Pro Asp Gln Pro Glu Phe His Gln Ala Val Glu Glu Val Leu Arg Ser
            20                  25                  30

Leu Trp Pro Phe Leu Glu Ala Asn Pro Arg Tyr Leu Thr Ser Gly Ile
        35                  40                  45

Leu Glu Arg Ile Cys Glu Pro Glu Arg Ala Ile Val Phe Arg Val Ser
    50                  55                  60

Trp Val Asp Asp Gln Gly Lys Val Gln Val Asn Arg Gly Phe Arg Ile
65                  70                  75                  80

Gln Met Asn Ser Ala Ile Gly Pro Tyr Lys Gly Gly Leu Arg Phe His
                85                  90                  95

Pro Ser Val Asn Leu Gly Val Leu Lys Phe Leu Ala Phe Glu Gln Thr
            100                 105                 110

Phe Lys Asn Ser Leu Thr Ser Leu Pro Met Gly Gly Gly Lys Gly Gly
        115                 120                 125

Ser Asp Phe Asp Pro Lys Gly Lys Ser Asp Ala Glu Val Met Arg Phe
    130                 135                 140

Cys Gln Ala Phe Met Ser Glu Leu Tyr Arg His Ile Gly Ala Asp Val
145                 150                 155                 160

Asp Val Pro Ala Gly Asp Ile Gly Val Gly Ala Arg Glu Ile Gly Phe
                165                 170                 175

Leu Phe Gly Gln Tyr Lys Arg Leu Ser Asn Gln Phe Thr Ser Val Leu
            180                 185                 190

Thr Gly Lys Gly Pro Ser Tyr Gly Gly Ser Leu Ile Arg Pro Glu Ala
        195                 200                 205
```

```
Thr Gly Phe Gly Cys Val Tyr Phe Ala Glu Glu Met Leu Lys Arg Arg
        210                 215                 220
Gly Glu Thr Val Glu Gly Lys Arg Val Ala Ile Ser Gly Ser Gly Asn
225                 230                 235                 240
Val Ala Gln Tyr Ala Ala Arg Lys Val Met Asp Leu Gly Gly Lys Val
                245                 250                 255
Ile Ser Leu Ser Asp Ser Glu Gly Thr Leu Tyr Cys Glu Ser Gly Leu
            260                 265                 270
Thr Glu Ala Gln Trp Gln Ala Val Leu Glu Leu Lys Asn Val Gln Arg
        275                 280                 285
Gly Arg Ile Ser Glu Leu Ala Gly Arg Phe Gly Leu Glu Phe Leu Ala
290                 295                 300
Gly Gln Arg Pro Trp Gly Leu Ser Cys Asp Ile Ala Leu Pro Cys Ala
305                 310                 315                 320
Thr Gln Asn Glu Leu Asp Ala Glu Ala Arg Ala Leu Leu Arg Asn
                325                 330                 335
Gly Cys Thr Cys Val Ala Glu Gly Ala Asn Met Pro Thr Thr Leu Glu
            340                 345                 350
Ala Val Asp Leu Phe Ile Glu Ala Gly Ile Leu Phe Ala Pro Gly Lys
        355                 360                 365
Ala Ser Asn Ala Gly Gly Val Ala Val Ser Gly Leu Glu Met Ser Gln
370                 375                 380
Asn Ala Met Arg Leu Leu Trp Thr Gly Gly Glu Val Asp Ser Lys Leu
385                 390                 395                 400
His Ala Ile Met Gln Ser Ile His His Ala Cys Val His Tyr Gly Glu
                405                 410                 415
Glu Asn Gly Gln Val Asn Tyr Val Lys Gly Ala Asn Ile Ala Gly Phe
        420                 425                 430
Val Lys Val Ala Asp Ala Met Leu Ala Gln Gly Val Val
        435                 440                 445

<210> SEQ ID NO 7
<211> LENGTH: 1341
<212> TYPE: DNA
<213> ORGANISM: Pseudomonas saudiphocaensis

<400> SEQUENCE: 7
atgatcgaaa ctgttgatgc cttccttgct cgcttacgtc aacgtgaccc ccaccaaccc    60
gagttccacc aggctgtaga agaggtggtc cgtagcctgt ggccattcct ggaggccaat   120
ccgcgctaca tgcaggctgg gattatcgag cgcatggtcg aacctgaacg cgcgatcatg   180
ttccgtgttc cgtgggtgga tgatcagggc cgtgtacaag taaatcgtgg ttaccgcatc   240
cagatgaatt cagccatcgg accgtataaa ggaggcctgc gtttccatcc atcagtaaac   300
gtcggggtgt tgaaatttct ggcttttgag caagtcttca agaactccct tacctctttg   360
ccaatgggag gaggaaaggg agggagcgac ttcaatccaa aggtaaatc cgataacgag    420 gtcatgcgct tctgtcaatc atttatgtct gaattgtacc gccacatcgg cgccgatttg   480
gacgttcccg ccggggacat tggtgttggc ggccgtgaga tcggcttcct ttttggccaa   540
tataaacgcc tgtcaaacca gtttacaagt gtgttgaccg ggaaaggcct tgcatacgga   600
ggaagcctta ttcgtcctga ggctacgggg tacggctgcg tgtattttgc gcaagaaatg   660
ttgaagagta cacgcagttc cttcgagggg aagcgcgttt caatttcggg tagcggaaat   720
gtcgcccaat atgctgcgca aaggtcatc gaattaggag gcctggtagt tagcgtgagc    780
```

-continued

```
gattccggtg gtacattaca cttccccgat ggcatgaccg aagaacagtg ggagtacctg      840
atggacttaa agaatgttcg tcgcggtcgc cttgaagaga tgggagcaca tttcggcgtc      900
acgtatatgc ctgaccaacg cccatggtcc cttccctgcg catcgccctt accatgtgcc      960
actcagaatg aattagacgg cgacgatgcc cgcacgttac tgaagaatgg gtgcttctgt     1020
gtggcggaag gtgcaaatat gccctctacc ctggaagctg tcgatctgtt cttggaagct     1080
ggaatcctgt acgctcctgg taaagcctct aatgccgggg gagttgcatg cagcgggtta     1140
gagatgtccc agaacagtat gcgtctgcac tggacggcgg gggaagtcga cactaaactg     1200
cattccatca tgcaatctat ccatcatgcc tgcgtcgctt acggcgaaga ggaggatggt     1260
cgtatcaatt acgtcaaagg tgctaatatc gcaggtttcg tcaaagtggc agacgctatg     1320
cttgcccaag gagtcgttta a                                               1341
```

<210> SEQ ID NO 8
<211> LENGTH: 446
<212> TYPE: PRT
<213> ORGANISM: Pseudomonas saudiphocaensis

<400> SEQUENCE: 8

```
Met Ile Glu Thr Val Asp Ala Phe Leu Ala Arg Leu Arg Gln Arg Asp
1               5                   10                  15

Pro His Gln Pro Glu Phe His Gln Ala Val Glu Glu Val Val Arg Ser
            20                  25                  30

Leu Trp Pro Phe Leu Glu Ala Asn Pro Arg Tyr Met Gln Ala Gly Ile
        35                  40                  45

Ile Glu Arg Met Val Glu Pro Glu Arg Ala Ile Met Phe Arg Val Pro
    50                  55                  60

Trp Val Asp Asp Gln Gly Arg Val Gln Val Asn Arg Gly Tyr Arg Ile
65                  70                  75                  80

Gln Met Asn Ser Ala Ile Gly Pro Tyr Lys Gly Gly Leu Arg Phe His
                85                  90                  95

Pro Ser Val Asn Val Gly Val Leu Lys Phe Leu Ala Phe Glu Gln Val
            100                 105                 110

Phe Lys Asn Ser Leu Thr Ser Leu Pro Met Gly Gly Gly Lys Gly Gly
        115                 120                 125

Ser Asp Phe Asn Pro Lys Gly Lys Ser Asp Asn Glu Val Met Arg Phe
    130                 135                 140

Cys Gln Ser Phe Met Ser Glu Leu Tyr Arg His Ile Gly Ala Asp Leu
145                 150                 155                 160

Asp Val Pro Ala Gly Asp Ile Gly Val Gly Gly Arg Glu Ile Gly Phe
                165                 170                 175

Leu Phe Gly Gln Tyr Lys Arg Leu Ser Asn Gln Phe Thr Ser Val Leu
            180                 185                 190

Thr Gly Lys Gly Leu Ala Tyr Gly Gly Ser Leu Ile Arg Pro Glu Ala
        195                 200                 205

Thr Gly Tyr Gly Cys Val Tyr Phe Ala Gln Glu Met Leu Lys Ser Thr
    210                 215                 220

Arg Ser Ser Phe Glu Gly Lys Arg Val Ser Ile Ser Gly Ser Gly Asn
225                 230                 235                 240

Val Ala Gln Tyr Ala Ala Gln Lys Val Ile Glu Leu Gly Gly Leu Val
                245                 250                 255

Val Ser Val Ser Asp Ser Gly Gly Thr Leu His Phe Pro Asp Gly Met
            260                 265                 270
```

-continued

```
Thr Glu Glu Gln Trp Glu Tyr Leu Met Asp Leu Lys Asn Val Arg Arg
            275                 280                 285

Gly Arg Leu Glu Glu Met Gly Ala His Phe Gly Val Thr Tyr Met Pro
        290                 295                 300

Asp Gln Arg Pro Trp Ser Leu Pro Cys Asp Ile Ala Leu Pro Cys Ala
305                 310                 315                 320

Thr Gln Asn Glu Leu Asp Gly Asp Ala Arg Thr Leu Leu Lys Asn
                325                 330                 335

Gly Cys Phe Cys Val Ala Glu Gly Ala Asn Met Pro Ser Thr Leu Glu
            340                 345                 350

Ala Val Asp Leu Phe Leu Glu Ala Gly Ile Leu Tyr Ala Pro Gly Lys
            355                 360                 365

Ala Ser Asn Ala Gly Gly Val Ala Cys Ser Gly Leu Glu Met Ser Gln
        370                 375                 380

Asn Ser Met Arg Leu His Trp Thr Ala Gly Glu Val Asp Thr Lys Leu
385                 390                 395                 400

His Ser Ile Met Gln Ser Ile His His Ala Cys Val Ala Tyr Gly Glu
                405                 410                 415

Glu Glu Asp Gly Arg Ile Asn Tyr Val Lys Gly Ala Asn Ile Ala Gly
            420                 425                 430

Phe Val Lys Val Ala Asp Ala Met Leu Ala Gln Gly Val Val
            435                 440                 445

<210> SEQ ID NO 9
<211> LENGTH: 445
<212> TYPE: PRT
<213> ORGANISM: Pseudomonas moorei

<400> SEQUENCE: 9

Met Ile Glu Ser Val Glu Ser Phe Leu Ala Phe Leu Lys Lys Phe Asp
1               5                   10                  15

Pro Asp Gln Pro Glu Phe His Gln Ala Val Glu Glu Val Leu Phe Ser
            20                  25                  30

Leu Trp Pro Phe Leu Glu Ala Asn Pro Phe Tyr Leu Thr Ser Gly Ile
        35                  40                  45

Leu Glu Phe Ile Cys Glu Pro Glu Phe Ala Ile Val Phe Val Ser
    50                  55                  60

Trp Val Asp Asp Gln Gly Lys Val Gln Val Asn Phe Gly Phe Ile
65                  70                  75                  80

Gln Met Asn Ser Ala Ile Gly Pro Tyr Lys Gly Gly Leu Phe His
                85                  90                  95

Pro Ser Val Asn Leu Gly Val Leu Lys Phe Leu Ala Phe Glu Gln Thr
            100                 105                 110

Phe Lys Asn Ser Leu Thr Ser Leu Pro Met Gly Gly Lys Gly Gly
        115                 120                 125

Ser Asp Phe Asp Pro Lys Gly Lys Ser Asp Ala Glu Val Met Phe Phe
    130                 135                 140

Cys Gln Ala Phe Met Ser Glu Leu Tyr Phe His Ile Gly Ala Asp Val
145                 150                 155                 160

Asp Val Pro Ala Gly Asp Ile Gly Val Gly Ala Phe Glu Ile Gly Phe
                165                 170                 175

Leu Phe Gly Gln Tyr Lys Phe Leu Ser Asn Gln Phe Thr Ser Val Leu
            180                 185                 190

Thr Gly Lys Gly Pro Ser Tyr Gly Gly Ser Leu Ile Phe Pro Glu Ala
        195                 200                 205
```

Thr Gly Phe Gly Cys Val Tyr Phe Ala Glu Glu Met Leu Lys Phe Phe
    210                 215                 220

Gly Glu Thr Val Glu Gly Lys Phe Val Ala Ile Ser Gly Ser Gly Asn
225                 230                 235                 240

Val Ala Gln Tyr Ala Ala Phe Lys Val Met Asp Leu Gly Gly Lys Val
                245                 250                 255

Ile Ser Leu Ser Asp Ser Glu Gly Thr Leu Tyr Cys Glu Ser Gly Leu
            260                 265                 270

Thr Glu Ala Gln Trp Gln Ala Val Leu Glu Leu Lys Asn Val Gln Phe
        275                 280                 285

Gly Phe Ile Ser Glu Leu Ala Gly Phe Gly Leu Glu Phe Leu Ala
    290                 295                 300

Gly Gln Phe Pro Trp Gly Leu Ser Cys Asp Ile Ala Leu Pro Cys Ala
305                 310                 315                 320

Thr Gln Asn Glu Leu Asp Ala Glu Ala Phe Ala Leu Leu Phe Asn
                325                 330                 335

Gly Cys Thr Cys Val Ala Glu Gly Ala Asn Met Pro Thr Thr Leu Glu
            340                 345                 350

Ala Val Asp Leu Phe Ile Glu Ala Gly Ile Leu Phe Ala Pro Gly Lys
        355                 360                 365

Ala Ser Asn Ala Gly Gly Val Ala Val Ser Gly Leu Glu Met Ser Gln
    370                 375                 380

Asn Ala Met Phe Leu Leu Trp Thr Gly Gly Glu Val Asp Ser Lys Leu
385                 390                 395                 400

His Ala Ile Met Gln Ser Ile His His Ala Cys Val His Tyr Gly Glu
                405                 410                 415

Glu Asn Gly Gln Val Asn Tyr Val Lys Gly Ala Asn Ile Ala Gly Phe
            420                 425                 430

Val Lys Val Ala Asp Ala Met Leu Ala Gln Gly Val Val
        435                 440                 445

<210> SEQ ID NO 10
<211> LENGTH: 789
<212> TYPE: DNA
<213> ORGANISM: Exiguobacterium sibiricum

<400> SEQUENCE: 10
atgggttata attctctgaa aggcaaagtc gcgattgtta ctggtggtag catgggcatt    60
ggcgaagcga tcatccgtcg ctatgcagaa gaaggcatgc gcgttgttat caactatcgt   120
agccatccgg aggaagccaa aaagatcgcc gaagatatta acaggcaggt ggtgaagcc    180 ctgaccgtcc agggtgacgt ttctaaagag gaagacatga tcaacctggt gaaacagact   240
gttgatcact tcggtcagct ggacgtcttt gtgaacaacg ctggcgttga atgccttct    300 ccgtcccacg aaatgtccct ggaagactgg cagaaagtga tcgatgttaa ctgacgggt    360 gcgttcctgg cgctcgtga agctctgaaa tacttcgttg aacataacgt gaaaggcaac   420
attatcaata tgtctagcgt ccacgaaatc atcccgtggc ctactttcgt acattacgct   480
gcttctaagg gtggcgttaa actgatgacc cagactctgg ctatggaata tgcaccgaaa   540
ggtatccgca ttaacgctat cggtccaggc gcgatcaaca ctccaattaa tgcagaaaaa   600
ttcgaggatc cgaaacagcg tgcagacgtg gaaagcatga tcccgatggg caacatcggc   660

```
aagccagagg agatttccgc tgtcgcggca tggctggctt ctgacgaagc gtcttacgtt    720
accggcatca ccctgttcgc agatggtggc atgaccctgt acccgagctt tcaggctggc    780
cgtggttga                                                            789
```

METHOD FOR THE PRODUCTION OF GLUFOSINATE-AMMONIUM

REFERENCE TO AN ELECTRONIC SEQUENCE LISTING

The content of the electronic sequence listing (2024-01-25-SequenceListing.txt; Size: 32,169 bytes; and Date of Creation: Jan. 25, 2024) is herein incorporated by reference in its entirety.

TECHNICAL FIELD

The present invention relates to the field of biochemical industry, and specifically relates to a production method of homochiral L-glufosinate-ammonium, which is a method for producing optically pure L-glufosinate-ammonium using a glufosinate-ammonium dehydrogenase mutant derived from microorganisms.

BACKGROUND ART

Glufosinate-ammonium is the second largest herbicide that transgenic crops are resistant to in the world. It was developed and produced by Hearst Corporation (now owned by Bayer after several mergers). Its chemical name is 4-[hydroxy (methyl) phosphonoyl]-DL-homoalanine, also known as glufosinate ammonium salt, Basta, Buster, etc.. It is a phosphonic acid herbicide, a glutamine synthetase inhibitor and a nonselective (killing), contact herbicide.

At present, three major herbicides in the world are glyphosate, glufosinate and paraquat. Compared with paraquat and glyphosate, glufosinate has excellent herbicidal performance and less side-effect to crops. With glufosinate-tolerant transgenic crops developed rapidly, market demand for glufosinate-ammonium will be huge in the future, and the prospects are very broad.

Glufosinate-ammonium has two optical isomers, L-glufosinate-ammonium and D-glufosinate-ammonium. However, only the L-configuration has the features of physiological activity, easy decomposability in soil and less toxicity to humans and animals, is a broad-spectrum herbicide, and is less destructive to environment.

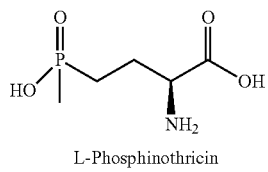

L-Phosphinothricin

Glufosinate-ammonium has two enantiomers, D and L, but only the L-configuration has the features of phytotoxicity, easy decomposability in the soil and less toxicity to humans and animals, and is less destructive to environment. At present, glufosinate-ammonium on the market is generally a racemic mixture. If glufosinate-ammonium products can be used in the form of optically pure L-isomer, the amount of glufosinate-ammonium applied can be reduced by 50%, which is very important for improving atomic economy and reducing the cost and environmental pressure. The currently reported methods to produce L-glufosinate-ammonium are mainly chemical synthesis methods including resolution of racemic glufosinate-ammonium, chiral pool method, chiral auxiliary group method and asymmetric catalysis method. However, they have problems that D-glufosinate-ammonium is not easy to racemize and reuse, that the synthesis steps are lengthy, that the reaction requires ultra-low temperature, that the product ee value is low, that the yield is low, and that the chiral resolution reagents are expensive. In contrast, biosynthesis has the advantages of strict stereoselectivity, mild reaction conditions, and easy separation and purification of products. Therefore, exploring the feasibility of using biosynthesis to produce L-glufosinate-ammonium has very important industrial value and significant social benefits.

According to raw materials and methods, biological methods of producing L-glufosinate-ammonium mainly include the following three categories:

1) Using L-glufosinate-ammonium derivative as a substrate, obtain L-glufosinate-ammonium by enzymatic hydrolysis directly. The main advantages are high conversion rate and high ee value of the product, but it is expensive and difficult to obtain chiral raw materials as precursors (Organophosphorus analogues and derivatives or the natural L-amino carboxylic acids and peptides. I. Enzymatic synthesis or D-, DL-, and L-phosphinothricin and their cyclicanalogues[J]. BµLlchemsocjpn, 1988, 61(10):3699-3704.). For example, the simplest biological method to prepare L-glufosinate-ammonium is to directly hydrolyze bialaphos by a protease. Bialaphos is a natural tripeptide. Under the catalysis of the protease, bialaphos removes 2 molecules of L-alanine to generate L-glufosinate-ammonium.

2) Using precursor of racemic glufosinate-ammonium as a substrate, obtain L-glufosinate-ammonium by enantioselective hydrolysis of an enzyme. The main advantage is that raw materials are relatively easy to obtain, and that the catalyst has high activity, but its theoretical yield can only reach 50%, which will cause waste of raw materials. Natchev reported a method to prepare L-glufosinate-ammonium by using a-chymotrypsin to hydrolyze the ethyl ester of bialaphos. The method firstly undergoes a 3-step reaction to transform racemic glufosinate into the diethyl ester of bialaphos, secondly selectively hydrolyzes of the C-terminal ester group of the diethyl ester of bialaphos by alkaline mesintericopeptidase, thirdly undergoes a-chymotrypsin-catalyzed hydrolysis of the peptide bond (ChemInrormAbstract: Total Synthesis and Enzyme-Substrate Interaction or D-, DL-, and L-Phosphinotricine, "Bialaphos" (Sr-1293) and Its Cyclic Analogues[J].ChemInrorm,1989, 1(17):125-131.), in which, the a-chymotrypsin can selectively hydrolyze the ethyl ester of L-bialaphos to produce the ethyl ester of L-glufosinate-ammonium, and finally use phosphodiesterase to hydrolyze P-terminal ester group to obtain L-glufosinate-ammonium.

3) Using a-keto acid-2-carbonyl-4-[(hydroxy)(methyl)phosphinoyl]-butyric acid as a substrate, obtain L-glufosinate-ammonium by asymmetric synthesis of enzymes, mainly including transaminase and glufosinate-ammonium dehydrogenase. When studying metabolic pathways of glufosinate-ammonium in soil microorganisms, researchers have already found that transaminase decomposes L-glufosinate-ammonium into a-keto acid-2-carbonyl-4-[(hydroxy)(methyl)phosphinoyl]-butyric acid (PPO for short) by transamination. In the 1990s, SchµLz A et al. (Stereospecific production or the herbicide phosphinothricin (glufosinate) by transamination: isolation and characterization of a phosphinothricin-specific transaminase from

*Escherichia coli*[J].Applied& Environmental Microbiology, 1990, 56(1):1-6.) have already used a transaminase cloned from *E. coli* to catalyze transamination to produce L-glufosinate-ammonium using 2-carbonyl-4-[(hydroxy)(methyl)phosphinoyl]-butyric acid as a substrate and L-glutamic acid as an amino donor. Immobilize the transaminase and install it in a bioreactor to catalyze preparation of L-glufosinate-ammonium, the product concentration can reach 76.1 g/L, the highest yield is 50 g/(L·h), the ee value of L-glufosinate-ammonium exceeds 99.9%. However, using transaminase to prepare L-glufosinate-ammonium has two major drawbacks, one is that the raw material PPO cannot be completely converted into L-PPT, and the maximum conversion rate is only 90%; the second is that it requires more than 4 times the equivalent of L-glutamic acid as amino donor to make the reversible reaction proceed in the direction of generating L-PPT, and that the excess glutamic acid brings great trouble to the separation of L-glufosinate-ammonium.

In many enzymatic synthesis routes of glufosinate-ammonium, ketone carbonyl group of a keto acid intermediate is a prochiral group, which can construct a chiral center through an enzymatic synthesis route. The keto acid route has also become a suitable route for industrial development and production of L-glufosinate-ammonium because the raw materials are cheap and easy to obtain and it avoid highly toxic cyanide.

Glufosinate-ammonium dehydrogenase (EC 1.4.1.-, AADH) is an enzyme that can reversibly deaminate amino acids to produce corresponding keto acids, and the reaction requires participation of nucleoside coenzymes (NAD(P)+). According to its substrate specificity, it can be divided into glufosinate-ammonium dehydrogenase, leucine dehydrogenase, alanine dehydrogenase, valine dehydrogenase and so on. Because of its excellent catalytic efficiency and selectivity, glufosinate-ammonium dehydrogenase is widely used in the synthesis of natural and unnatural a-amino acids. For instance, Li et al. used leucine dehydrogenase to prepare L-tert-leucine, 0.6M substrate was completely converted within 5.5 h, and the ee value of the product reached 99% (Stereoselective synthesis or L-tert-leucine by a newly cloned leucine dehydrogenase from *Exiguobacterium sibiicum*[J].Journal or Molecular Catalysis B Enzymatic, 2014, 105(7):11-17.). Hanson et al. used glufosinate-ammonium dehydrogenase to prepare L-6-hydroxynorleucine, the final yield was 91-97% and the ee value was greater than 99% (Enzymatic synthesis or L-6-hydroxynorleucine.[J]. Bioorganic & Medicinal Chemistry, 1999, 7(10): 2247-2252.).

We cloned a glufosinate-ammonium dehydrogenase gene from *Pseudomonas moorei* WP_090325311.1, and realized heterologous expression of the gene in *Escherichia coli*. The enzyme can catalyze the asymmetric reductive amination of 2-carbonyl-4-[(hydroxy)(methyl)phosphinoyl]-butyric acid to produce L-glufosinate-ammonium. However, the activity of this wild-type enzyme on 2-carbonyl-4-[(hydroxy)(methyl)phosphinoyl]-butyric acid was not high enough, which limited its industrial application. Based on the reported crystal structure of the glufosinate-ammonium dehydrogenase, we used molecular simulations to determine the spatial structure of the enzyme and possible glufosinate-ammonium sites related to activity, and used site-directed mutagenesis technique to improve catalytic activity of the glufosinate-ammonium dehydrogenase on 2-carbonyl-4-[(hydroxy)(methyl)phosphinoyl]-butyric acid, so the enzyme will have stronger industrial application value.

SUMMARY OF THE INVENTION

Aiming at the problems that the existing glufosinate-ammonium dehydrogenases showed low activity and low substrate concentration on the asymmetric reductive amination of 2-carbonyl-4-[(hydroxy)(methyl)phosphinoyl]-butyric acid, the present invention provides a glufosinate-ammonium dehydrogenase mutant, a recombinant strain containing the glufosinate-ammonium dehydrogenase mutant gene and a crude enzyme solution thereof, wherein the recombinant strain and the crude enzyme solution are used as a biocatalyst for chiral biosynthesis of L-glufosinate-ammonium to make activity of the catalyst increased by nearly 10 times, and the substrate concentration increased by 5 times. Finally, 90 g/L 2-carbonyl-4-[(hydroxy)(methyl) phosphinoyl]-butyric acid can be completely catalyzed to produce L-glufosinate-ammonium within only 40 minutes (transaminases usually take 40 hours), and the ee value was greater than 99%. The method has high conversion rate of raw materials, high yield, and easy separation and purification of products.

Technical solutions adopted in the present invention are as follows:

The present invention provides a glufosinate-ammonium dehydrogenase mutant, wherein the glufosinate-ammonium dehydrogenase mutant is obtained by single- or multi-site mutation of the amino acids at position 107, 188, 239, 357 of the amino acid sequence shown in SEQ ID No. 6.

Further, the mutant is obtained by: mutating leucine at position 107 into arginine (L 107R), mutating leucine at position 107 into arginine+phenylalanine at position 188 into proline (L107R-F188P), mutating leucine at position 107 into arginine+glycine at position 239 into lysine (L107R-G239K), mutating leucine at position 107 into arginine+phenylalanine at position 188 into proline+glycine at position 239 into tyrosine(L107R-F188P-G239Y), mutating leucine at position 107 into arginine+phenylalanine at position 188 into proline+glycine at position 239 into cysteine (L107R-F188P-G239C), mutating leucine at position 107 into arginine+phenylalanine at position 188 into proline+glycine at position 239 into lysine (L107R-F188P-G239K), or mutating leucine at position 107 into arginine+phenylalanine at position 188 into proline+glycine at position 239 into lysine+phenylalanine at position 357 into glycine (L107R-F188P-G239K-F357G), preferably the mutant is L107R-F188P-G 239K-F357G.

The present invention also relates to an encoding gene and an engineered strain of the glufosinate-ammonium dehydrogenase mutant.

The present invention also provides an application of the glufosinate-ammonium dehydrogenase mutant in catalyzing 2-carbonyl-4-[(hydroxy)(methyl)phosphinoyl]-butyric acid to produce L-glufosinate-ammonium, and the application is carried out as follows: put wet cells or a crude enzyme solution as a catalyst, 2-carbonyl-4-[(hydroxy)(methyl) phosphinoyl]-butyric acid as a substrate, glucose as a cosubstrate and an inorganic amino donor into a pH 7.5 buffer to construct a conversion system, carry out the reaction at 35° C. and 600 rpm, after reacting completely, subject the reaction solution to separation and purification, thereby obtaining L-glufosinate-ammonium; in which, the wet wells are obtained by fermentation culture of the recombinant engineered strain containing a gene of the glufosinate-ammonium dehydrogenase mutant and a gene of a glucose dehydrogenase, and the crude enzyme solution is obtained by subjecting the wet cells to ultrasonic disintegration. In the conversion system, the amount of the catalyst calculated by the weight of the wet cells is 20-100 g/L (20-100 g of the wet cells/L buffer), the initial concentration of the substrate is 10-500 mM, the concentration of the glucose is 12-600 mM, and the concentration of the inorganic amino donor is 50 mM-1.5M; the inorganic amino donor is preferably $(NH_4)_2SO_4$.

In the reaction system of the present invention, the catalyst may be used in the form of a crude enzyme solution of broken cells, resting cells of the engineered strain expressing the recombinant enzyme, a purified enzyme or an immobilized enzyme.

The catalyst of the present invention is prepared by a method as follows: the recombinant strain E. coli BL21 (DE3)/pETDuet-1-PPTGDH E3-GDH containing glucose dehydrogenase and glufosinate-ammonium dehydrogenase E3 is inoculated into LB liquid medium containing 50 μg/mL ampicillin and incubated at 37° C. and 200 rpm for 12 hours; the resulting inoculum is inoculated with 1% (v/v) incubating volume to fresh LB liquid medium containing 50 u g/mL ampicillin and incubated at 37° C. and 150 rpm; when OD600=0.6-0.8 is achieved, IPTG is added with a final concentration of 24 μg/mL, and the bacteria solution is subjected to induced expression at 18° C. for 16 hours; the resulting fermentation broth is subjected to centrifugation at 37° C. and 8000 rpm for 20 min, the supernatant is discarded, and the pellet is collected and washed twice with a pH 7.5, 20 mM phosphate buffer (PBS), thereby obtaining the wet cells; the wet cells are resuspended with pH 7.5, 100 mM PBS and subjected to ultrasonic disintegration in an ice-water mixture for 10 min, and the conditions of the ultrasonic disintegration are 400 W and is on, 5 s off, thereby obtaining a crude enzyme solution.

The glucose dehydrogenase of the present invention is derived from *Exiguobacterium sibiricum*, and the NCBI accession number is KM817194.1 (the nucleotide sequence is shown in SEQ ID No. 10), the gene of the glucose dehydrogenase is linked to pET-28b(+) vector by double digests, and the recombinant plasmid is introduced into *E. coli* BL21(DE3), thereby obtaining the recombinant glucose dehydrogenase strain *E. coli* BL21(DE3)/pET28b-GDH.

Compared with prior art, advantages of the present invention are embodied in:
(1) The method in the present invention uses 2-carbonyl-4-[(hydroxy)(methyl)phosphinoyl]-butyric acid or its salts as a substrate, the glufosinate-ammonium dehydrogenase directly catalyzes the reductive amination of the substrate with an inorganic amino donor and a coenzyme, thereby obtaining homochiral L-glufosinate-ammonium. The activity of the catalyst can be increased by nearly 10 times, and the substrate concentration can be increased by 5 times. It takes only 40 minutes to completely catalyze 90 g/L 2-carbonyl-4-[(hydroxy)(methyl)phosphinoyl]-butyric acid to produce L-glufosinate-ammonium (while transaminases usually take 40 hours), and the ee value is greater than 99%. The method has features of high conversion rate of raw materials, high yield, easy separation and purification of the product, and high chiral purity.
(2) Compared with catalytic processes such as transaminase, the method in the present invention has features of relatively simple process, high conversion rate of raw materials, a conversion rate up to 100%, and easy separation and purification of the product from the reaction solution.

SPECIFIC EMBODIMENTS

Figure 1:
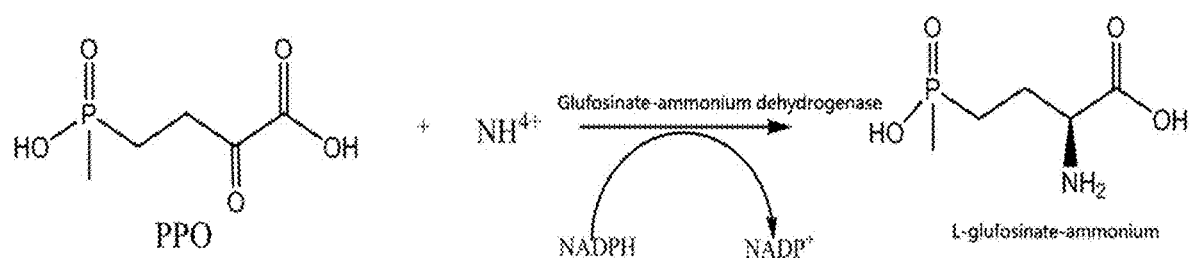
FIG. 1 is a reaction diagram showing that the glufosinate-ammonium dehydrogenase mutant catalyzes the asymmetric reductive amination of 2-carbonyl-4-[(hydroxy)(methyl) phosphinoyl]-butyric acid to obtain L-glufosinate-ammonium.
Figure 2:
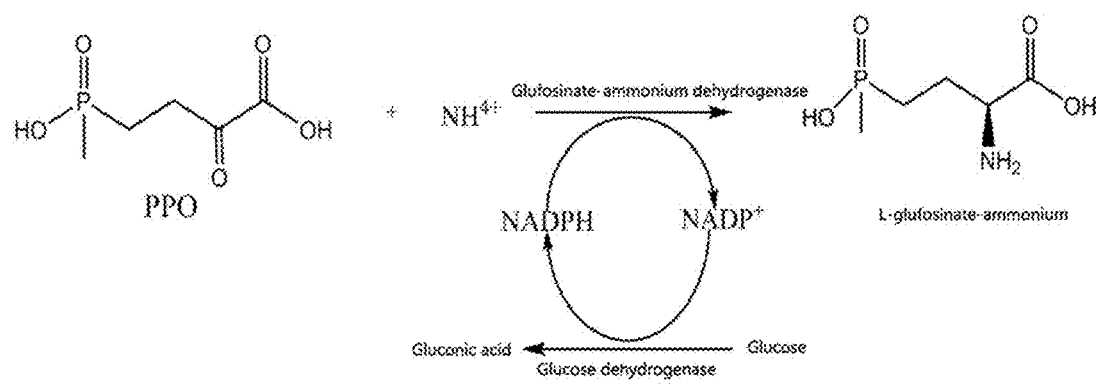
FIG. 2 is a reaction diagram showing that the glufosinate-ammonium dehydrogenase coupled with an enzyme that regenerates the coenzyme catalyzes the asymmetric reductive amination of 2-carbonyl-4-[(hydroxy)(methyl)phosphinoyl]-butyric acid to obtain L-glufosinate-ammonium.

The present invention is further illustrated below with specific examples. It should be understood that the following examples are only used to illustrate the present invention, not to limit the scope of the present invention.

Experimental methods in the present invention are conventional methods unless otherwise specified, and the specific gene cloning operations refer to the "Molecular Cloning: A Laboratory Manual" edited by J. Sambrook et al..

Reagents used in upstream genetic engineering operations: one-step cloning kits used in the examples of the present invention were purchased from Vazyme Biotech Co., Ltd., Nanjing; plasmid extraction kits and DNA extraction and purification kits were purchased from Axygen Co., Ltd., Hangzhou; *E. coli* BL21(DE3), plasmids, etc. were purchased from Sangon Biotech (Shanghai) Co., Ltd.; DNA marker, FastPfu DNA polymerase, low molecular weight protein standards, agarose electrophoresis reagents were purchased from Hangzhou Tsingke Biological Technology Co., Ltd.; and primer synthesis and gene sequencing were completed by Hangzhou tsingke Biological Technology Co., Ltd.. Refer to the product manual for the use of the above reagents.

Reagents used in downstream catalysis process: standard reagents 2-carbonyl-4-[(hydroxy)(methyl)phosphinoyl]-butyric acid (PPO), D,L-glufosinate-ammonium and L-glufosinate-ammonium were purchased from Sigma-Aldrich; NADPH was purchased from Bontac Bio-Engineering (Shenzhen) Co., Ltd.; and other common reagents were purchased from Sinopharm Chemical Reagent Co., Ltd..

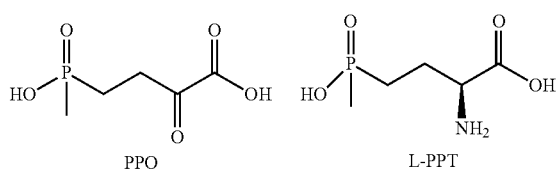

PPO                                L-PPT

Example 1 Construction of Expression Vectors and Engineering Strains

Based on literature reports and homology of gene sequence, 4 dehydrogenases derived from *Pseudomonas*, *Pseudomonas extemaustralis*, *Pseudomonas moor-i* and *Pseudomonas saudiphocaensis* respectively, were selected from NCBI database. Their NCBI accession numbers are WP_092488511.1, WP_010562566.1, WP_090325311.1 or WP_037025837.1, respectively. The gene sequences were subjected to whole gene synthesis to obtain four glufosinate-ammonium dehydrogenases, which were glufosinate-ammonium dehydrogenase E1 (the nucleotide sequence is shown in SEQ ID NO. 1, and the amino acid sequence is shown in SEQ ID NO. 2) derived from *Pseudomonas*, glufosinate-ammonium dehydrogenase E2 (the nucleotide sequence is shown in SEQ ID NO. 3, and the amino acid sequence is shown in SEQ ID NO. 4) derived from *Pseudomonas extremaustralis*, glufosinate-ammonium dehydrogenase E3 (the nucleotide sequence is shown in SEQ ID NO. 5, and the amino acid sequence is shown in SEQ ID NO. 6) derived from *Pseudomonas moorei* and glufosinate-ammonium dehydrogenase E4(the nucleotide sequence is shown in SEQ ID NO. 7, and the amino acid sequence is shown in SEQ ID NO. 8) derived from *Pseudomonas saudiphocaensis*.

Primers were designed according to the nucleotide sequences shown in SEQ ID NO. 1, SEQ ID NO. 3, SEQ ID NO. 5 and SEQ ID NO. 7, and restriction sites Sac I and Not I were added to the primers, respectively:

E1 upstream primer: 5'-GAGCTCATGATCGAATCCGTGGAA

TCA-3';

E1 downstream primer: 5'-GCGGCCGCTTACACGATTCCCTG

GGCA-3';

E2 upstream primer: 5'-GAGCTCATGATCGAATCTGTCGAA

AGT-3';

E2 downstream primer: 5'-GCGGCCGCTTATACAATGCCCTGA

GCAAG-3';

E3 upstream primer: 5'-GAGCTCATGATTGAGAGCGTCGAG

TCT-3';

E3 downstream primer: 5'-GCGGCCGCTTAGACGACCCCCTGT

GCC-3';

E4 upstream primer: 5'-GAGCTCATGATCGAAACTGTTGATG

CC-3';

E4 downstream primer: 5'-GCGGCCGCTTAAACGACTCCTTGG

GCAAG-3'.

Plasmid pETDuet-1 was used as an expression vector to construct *E. coli* BL21 (DE3)/pETDuet-1-PPTGDH:

Construction of expression plasmids: under initialization of the above primers, the genomes of *Pseudomonas*, *Pseudomonas extremaustralis*, *Pseudomonas moorei* and *Pseudomonas saudiphocaensis* were used as templates respectively, and high-fidelity Pfu DNA polymerase was used for amplification to obtain the gene sequences of glufosinate-ammonium dehydrogenases E1, E2, E3, and E4, respectively. After sequencing, restriction enzymes Sac I and Not I (Takara) were used to digest the amplified fragments, and T4 DNA ligase (Takara) was used to ligate the fragment and pETDuet-1 which had been digested by the same restriction enzymes to construct expression plasmids pETDuet-1-PPTGDHE1, pETDuet-1-PPTGDHE2, pETDuet-1-PPTGDHE3 and pETDuet-1-PPTGDHE4.

Construction of recombinant *E. coli*: the competent cells of *E. coli* BL21 (DE3) (Invitrogen) stored at −80° C. were kept in an ice bath at 0° C. for 10 minutes, added with 5 μL of plasmids pETDuet-1-PPTGDHE1, pETDuet-1-PPTGDHE2, pETDuet-1-PPTGDHE3 or pETDuet-1-PPTGDHE4 under a super-clean bench, kept in an ice bath at 0° C. for 30 minutes, subjected to heat shock in a water bath at 42° C. for 90 s, kept in an ice bath at 0° C. for 2 min, added with 600 μL of LB medium, and incubated at 37° C. for 1 h with horizontal shaking at 200 rpm. The resulting inoculum was spread on an LB plate containing 50 μg/ml ampicillin and incubated at 37° C. for 8-12 h, and then the single colonies were picked for sequencing to screen recombinant *E. coli* containing the recombinant expression vectors, *E. coli* BL21(DE3)/pETDuet-1-PPTGDHE1, *E. coli* BL21(DE3)/pETDuet-1-PPTGDHE2, *E. coli* BL21(DE3)/pETDuet-1-PPTGDHE3 and *E. coli* BL21(DE3)/pETDuet-1-PPTGDHE4, respectively.

Preparation of the competent cells: the strain *E. coli* BL21(DE3) preserved in a glycerol stock tube in a refrigerator at −80° C. was subjected to streak plate method on a non-antibiotic LB plate and cultivated at 37° C. for 10 h, thereby obtaining single colonies; some of the single colonies on the LB plate were picked and inoculated to a tube containing 5 mL of LB medium, and cultivated at 37° C. and 180 rpm for 9 h; 200 μL of the bacterial solution from the tube was inoculated to 50 mL of LB medium and further incubated at 37° C. and 180 rpm until OD600=0.4-0.6 was achieved; the resulting bacterial solution was pre-cooled on ice, taken into a sterilized centrifuge tube, placed on ice for 10 minutes, and centrifuged at 4° C. and 5000 rpm for 10 minutes; the supernatant was discarded while preventing bacterial contamination, the pellet was resuspended in a 0.1 mol/L pre-cooled $CaCl_2$ aqueous solution, placed on ice for 30 minutes and centrifuged at 4° C. and 5000 rpm for 10 minutes; the supernatant was discarded, the pellet was resuspended in a 0.1 mol/L pre-cooled $CaCl_2$ aqueous solution containing 15% glycerol; each 100 μL of the resuspended cells were taken into a 1.5 mL sterilized centrifuge tube and stored in a refrigerator at −80° C. for use.

Example 2: Induced Expression and SDS-PAGE Analysis of the Glufosinate-Ammonium Dehydrogenase and the Glucose Dehydrogenase 1, Wet cells containing the glufosinate-ammonium dehydrogenase: the recombinant strains *E. coli* BL21(DE3)/pETDuet-1-PPTGDHE1, *E. coli* BL21(DE3)/pETDuet-1-PPTGDHE2, *E. coli* BL21(DE3)/pETDuet-1-PPTGDHE3 and *E. coli* BL21(DE3)/pETDuet-1-PPTGDHE4 were respectively inoculated into LB liquid medium containing 50 μg/mL ampicillin, incubated at 37° C. and 200 rpm for 12 hours, the resulting inoculum was inoculated with 1% (v/v) incubating volume to fresh LB liquid medium containing 50 μg/mL ampicillin, incubated at 37° C. and 150 rpm until OD600=0.6-0.8 was achieved, added with IPTG at a final concentration of 0.1 mM, incubated at 18° C. for 16 h, and centrifuged at 4° C. and 8000 rpm for 20 min, the supernatant was discarded, and the pellet was collected and washed twice with a pH 7.5, 20 mM phosphate buffer (PBS), thereby obtaining wet cells of *E. coli* BL21(DE3)/pETDuet-1-

PPTGDHE1, *E. coli* BL21(DE3)/pETDuet-1-PPTGDHE2, *E. coli* BL21(DE3)/pETDuet-1-PPTGDHE3 and *E. coli* BL21(DE3)/pETDuet-1-PPTGDHE4 containing the corresponding glufosinate-ammonium dehydrogenase.

2, Wet cells containing glucose dehydrogenase: a glucose dehydrogenase gene derived from *Exiguobacterium sibiricum* (the NCBI accession number is KM817194.1) was inserted into pET-28b(+) by double digests, the resulting recombinant plasmid was introduced into *E. coli* BL21 (DE3), thereby obtaining a recombinant glucose dehydrogenase strain *E. coli* BL21(DE3)/pET28b-esgdh. The recombinant glucose dehydrogenase strain *E. coli* BL21 (DE3)/pET28b-esgdh was inoculated to LB liquid medium containing kanamycin at a final concentration of 50 µg/mL and cultivated at 37° C. for 9 hours. The resulting inoculum was inoculated with 3.5% incubating volume to 3 L of fermentation medium in a 5 L fermentor. The 5 L fermentation tank was firstly disassembled for cleaning. After the cleaning, the fermentation tank was added a small amount of water. After installation, the inoculation port was opened, and the blank fermentation tank was placed in a sterilization pot at 121° C. for 20 minutes. After the sterilization, the prepared medium was added to the fermentation tank, the air outlet and inlet were sealed, the fermentation tank was installed and sealed and the inoculation port was open. The fermentation tank and the prepared lactose as an inducer were put in a sterilization pot and sterilized at 115° C. for 30 minutes (lactose cannot be sterilized at 121° C.). The inoculation port of the sterilized fermentation tank was screwed and the sterilized fermentation tank was installed on the operating system, condensed water and air were passed (a sterile membrane must be installed on the air inlet pipe), the air outlet was inserted below the liquid level of the conical flask, and when the temperature of the medium dropped to 37° C., the fire trap was placed on the inoculation port, and the resulting seed liquid was inoculated to the fermentation tank. The bacteria were incubated at 37° C. and 500 rpm for about 3-4 hours and met the density requirement of OD 6-8. After the temperature of the fermentation tank was reduced to 28° C., lactose was added as an inducer with a final concentration of 16 g/L, and then the bacteria was incubated at 28° C. and 500 rpm for 12 h. The incubated bacteria were centrifuged at 8000 rpm for 10 min and washed twice with pH 7.5, 20 mM phosphate buffer (PBS) to obtain wet cells containing glucose dehydrogenase GDH; the fermentation medium composition was as follows: tryptone 45 g, yeast extract 36 g, sodium chloride 30 g, potassium dihydrogen phosphate 4.08 g, glycerol 45 g, dipotassium hydrogen phosphate trihydrate 6.84 g, ammonium sulfate 15 g, magnesium sulfate 1.125 g, defoamer 4 g, and 3 L of distilled water was added to dissolve.

LB medium: 10 g/L peptone, 5 g/L yeast extract, 10 g/L NaCl, the solvent is water, pH7.4.

LB solid medium: 10 g/L peptone, 5 g/L yeast extract, 10 g/L NaCl, 18 g/L agar, the solvent is water, pH7.4.

3, Standard enzyme activity detection system: 25 g/L lysis of wet cells, 100 mM substrate PPO, 10 mM coenzyme NADPH, 250 mM $(NH_4)_2SO_4$, the reaction medium is a pH 7.5 phosphate buffer, the total system is 400 µL. The enzyme activity unit (U) is defined as follows: under the standard conditions, the amount of enzyme required for producing 1 µmol L-glufosinate-ammonium in one minute is one enzyme activity unit, U.

Prepare a reaction solution according to the above standard enzyme activity detection system, react in a metal bath shaking reactor at 35° C. for 10 minutes, add 40 µL of 5M NaOH to terminate the reaction, and store the resulting sample on ice. After diluting the sample to a certain volume, use HPLC with pre-column derivatization to detect the concentration of the substrate L-glufosinate-ammonium, and calculate enzyme activities. The results are shown in Table 1.

The concentration of the substrate was detected by high performance liquid chromatography (HPLC), and the analysis method was as follows: Chromatographic column model: QS-C18, 5 µm, 4.6×250 mm. Mobile phase: 50 mM ammonium dihydrogen phosphate was dissolved in 800 mL ultrapure water, 10 mL tetrabutylammonium hydroxide (10%) was added, water was used to dilute it to 1000 mL, the pH was adjusted to 3.8 with phosphoric acid, the resulting solution was mixed with acetonitrile at a ratio of 88:12. The detection wavelength was 232 nm, and the flow rate was 1.0 mL/min. Column temperature: 40° C., the peak time of 2-carbonyl-4-[(hydroxy)(methyl)phosphinoyl]-butyric acid was 9.7 min.

The chiral analysis and concentration analysis of the product were carried out by high performance liquid chromatography with pre-column derivatization. The specific analysis methods were as follows:

(1) Chromatography conditions: Chromatographic column model: QS-C18, 5 µm, 4.6×250 mm. Mobile phase: 50 mM ammonium acetate solution: methanol=10:1. Fluorescence detection wavelength: λex=340 nm, λem=455 nm. Flow rate: 1 mL/min. Column temperature: 30° C., the peak time of L-glufosinate-ammonium was 8.5 min, and the peak time of D-glufosinate-ammonium was 10.2 min.

(2) Derivatization reagent: weigh 0.1 g of o-phthalaldehyde and 0.12 g of N-acetyl-L-cysteine respectively, use 10 mL of ethanol to assist dissolution, and then add 40 mL of a 0.1 moL/L boric acid buffer (pH 9.8), shake to fully dissolve, store in a refrigerator at 4° C. for use (not more than 4 days).

(3) Derivatization reaction and determination: add 100 µL of the sample with 400 µL of a derivatization reagent, shake on a shaker at 500 rpm and 30° C. for 5 minutes, then add 400 µL of ultrapure water to mix, and inject 10 µL of the resulting sample for HPLC analysis.

TABLE 1

Results of enzyme activity determination:

| Number | Enzyme activity U/g | Coenzyme | NCBI accession number | Origin |
|---|---|---|---|---|
| *E. coli* BL21(DE3)/pETDuet-1-PPTGDHE1 | 106.16 | NADPH | WP_092488511.1 | *Pseudomonas* sp. |
| *E. coli* BL21(DE3)/pETDuet-1-PPTGDHE2 | 101.32 | NADPH | WP_010562566.1 | *Pseudomonas extremaustralis* |

TABLE 1-continued

Results of enzyme activity determination:

| Number | Enzyme activity U/g | Coenzyme | NCBI accession number | Origin |
|---|---|---|---|---|
| E. coliBL21(DE3)/pETDuet-1-PPTGDHE3 | 180.37 | NADPH | WP_090325311.1 | Pseudomonas moorei |
| E. coli BL21(DE3)/pETDuet-1-PPTGDHE4 | 103.67 | NADPH | WP_037025837.1 | Pseudomonas saudiphocaensis |

According to the determination of enzyme activity, the enzyme activity of E. coli BL21(DE3)/pETDuet-1-PPTGDHE1 was 106.16 U/g, the enzyme activity of E. coli BL21(DE3)/pETDuet-1-PPTGDHE2 was 101.32 U/g, The enzyme activity of E. coli BL21(DE3)/pETDuet-1-PPTGDHE3 was 180.37 U/g, the enzyme activity of E. coli BL21(DE3)/pETDuet-1-PPTGDHE4 was 103.67 U/g, and E. coli BL21(DE3)/pETDuet-1-PPTGDHE3 had the highest enzyme activity.

Example 3 Glufosinate-Ammonium Dehydrogenase Mutant Catalyze PPO to Produce L-Glufosinate-Ammonium Crude enzyme solution: the wet cells containing the glufosinate-ammonium dehydrogenase and the wet cells containing the glucose dehydrogenase prepared by the method in Example 2 were resuspended in a pH 7.5, 100 mM PBS, and then the cells were subjected to ultrasonic disintegration in an ice-water mixture for 10 min, the conditions of the ultrasonic disintegration are 400 W, is on, and 5 s off, thereby obtaining a crude enzyme solution.

Figure 3:
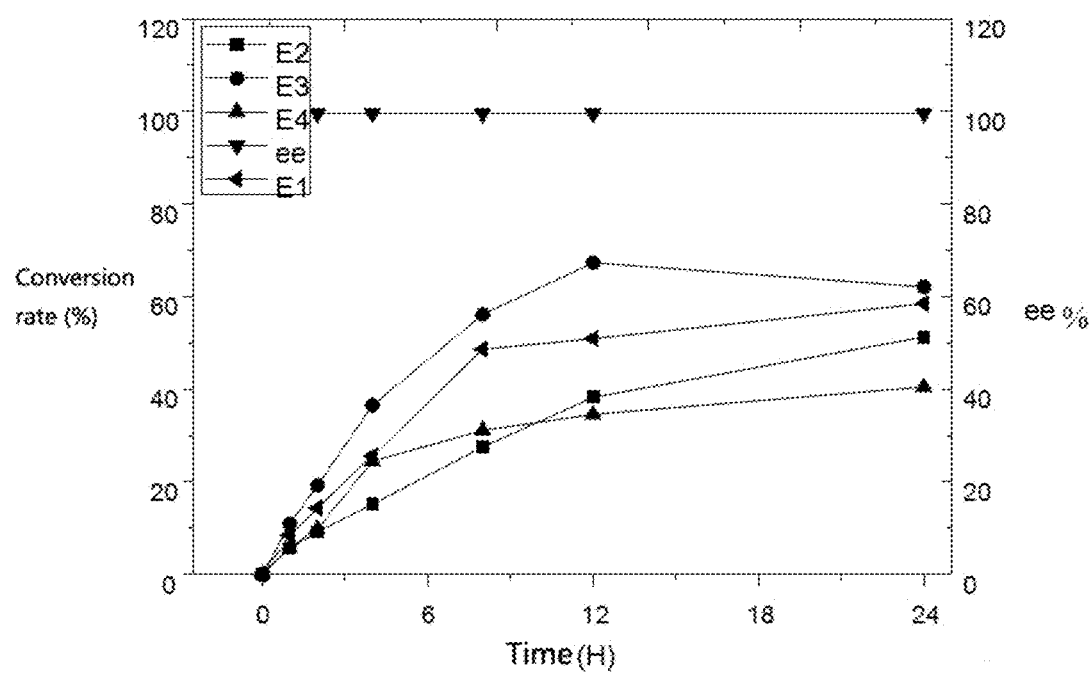
FIG. 3 is a reaction progress diagram of four wild-type strains, wherein the concentration of the substrate is 100 mmol/L, and the reaction time is 24 h.

Add the crude enzyme solution of glufosinate-ammonium dehydrogenase (the amount of the cells was 25 g/L buffer), 2-carbonyl-4-[(hydroxy)(methyl)phosphinoyl]-butyric acid (at a final concentration of 100 mmol/L), an inorganic amino donor $(NH_4)_2SO_4$ (at a final concentration of 500 mmol/L), glucose (at a final concentration of 120 mmol/L), NADPH (at a final concentration of 1 mmol/L) and the crude enzyme solution of GDH(the amount of the cells was 50 g/L buffer) in 30 mL of a PBS buffer (100 mM, pH 7.5) to construct a reaction system. React in a water bath at 35° C. for 24 hours, automatically adjust the pH with ammonia water to a constant 7.5, take samples at a regular time interval, and calculate the substrate conversion rate using the method in Example 2. The conversion rate of BL21(DE3)/pETDuet-1-PPTGDHE1 was 65.5%, the conversion rate of E. coli BL21(DE3)/pETDuet-1-PPTGDHE2 was 61.7%, the conversion rate of E. coli BL21(DE3)/pETDuet-1-PPTGDHE3 was 69.4%, the conversion rate of E. coli BL21(DE3)/pETDuet-1-PPTGDHE4 was 63.3%, and the ee value of the product was greater than 99%. The reaction process is shown in FIG. 3.

According to the determination of enzyme activity and reaction process, E. coli BL21(DE3)/pETDuet-1-PPTGDHE3 (WP_090325311.1) was finally selected as the strain to be modified for further experiment.

Example 4 Recombinant Strain E. coli BL21(DE3)/pETDuet-1-PPTGDHE3-GDH Containing Glucose Dehydrogenase and Glufosinate-Ammonium Dehydrogenase E3

1. Use one-step cloning to insert a gene of a glucose dehydrogenase into the second multiple cloning site of plasmid pETDuet-1:

Obtain a gene of a glucose dehydrogenase with homologous sequences: take sequences of 15-20 bp on both 5'- and 3'-end of the linearized vector as the homologous sequences and use E. coli BL21(DE3)/pET28b-GDH as template to design primer 1 and primer 2, add the homology arms to 5'-end of the gene-specific forward/reverse amplification primer sequence respectively, so as to amplify the gene of the glucose dehydrogenase with the homology arms using high fidelity Pfu DNA polymerase, after digesting the template, purify and recover the PCR product with a DNA recovery and purification kit, and measure the nucleic acid concentrations respectively, thereby obtaining the gene sequence of the glucose dehydrogenase containing homologous sequences which is shown in SEQ ID NO. 10.

```
Primer 1:
5'-GAGATATACATGGCAGATCTCATGGGTTATAATTCTCTGAAAGGCA
AAGTCGC-3';

Primer 2:
5'-GTGGCAGCAGCCTAGGTTAATTAATCAACCACGGCCAGCCTGAAAG
CTC-3'.
```

Homologous recombination reaction with a single fragment:

The optimal amount of cloning vector={0.02*base pairs of the cloning vector}ng(0.03 pmol)

The optimal amount of insert={0.04*base pairs of the insert}ng (0.06 pmol)

The reaction stem:

| Components | Recombination | Negative control-1 | Negative control-2 | Positive control |
|---|---|---|---|---|
| Linearized vector | X μL | X μL | 0 μL | 1 μL |
| N insert fragments | $Y_1 + Y_2 \ldots + Y_n$ μL | 0 μL | Y1 + Y2 . . . + $Y_n$ μL | 1 μL |
| 2*CLonExpressMIX | 5 μL | 0 μL | 0 μL | 5 μL |
| cldH$_2$O | to 10 μL | to 10 μL | to 10 μL | to 10 μL |

Note:
X represents the amount of linearized vector, and Y represents the amount of insert.

Figure 4:
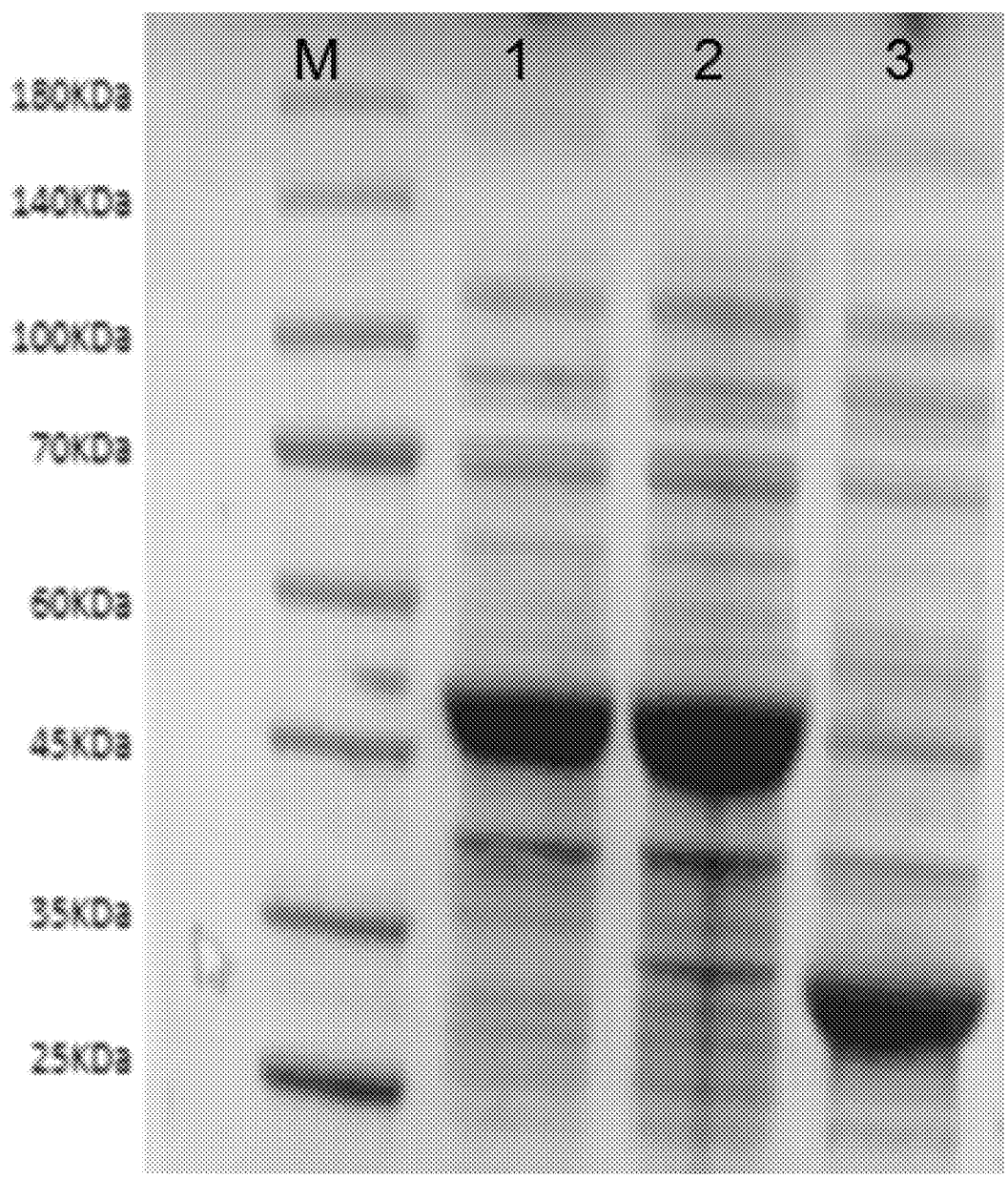
FIG. 4 is an SDS-PAGE diagram of the crude enzyme solution, wherein M: protein molecular weight standard, lane 1: the crude enzyme solution of the glufosinate-ammonium dehydrogenase BL21(DE3)/pETDuet-1-PPTGDHE3, lane 2: the crude enzyme solution of the recombinant strain *E. coli* BL21(DE3)/pETDuet-1-PPTGDHE3-GDH containing the glufosinate-ammonium dehydrogenase E3-glucose dehydrogenase, lane 3: the crude enzyme solution of *E. coli* BL21(DE3)/pET28b-GDH containing the glucose dehydrogenase.

Mix the prepared reaction system gently with a pipette, and collect the reaction solution at the bottom of the tube after a short centrifugation. Place the reaction system in a water bath at 50° C. for 5 minutes, and then immediately cool it on ice. Introduce it into *E. coli* BL21 (DE3) (42 C, 90 s), spread it on an LB plate containing 50 ti g/mL ampicillin, incubate at 37° C. for 12-16 hours, extract plasmids of random-selected clones for sequencing, identify and screen, thereby obtaining a recombinant strain *E. coli* BL21(DE3)/pETDuet-1-PPTGDHE3-GDH containing the glufosinate-ammonium dehydrogenase E3 and the glucose dehydrogenase. Use protein electrophoresis for verification as follows: resuspend the wet cells in a pH 7.5, 20 mM phosphate buffer (PBS), add a 2× SDS-loading Buffer, treat the mixture in a boiling water bath for 10 min, and then carry out SDS-PAGE analysis. SDS-PAGE settings: run for 70 min at 120 mV. See the identification result in FIG. 4, the brand in the second lane corresponding to the protein expressed by *E. coli* BL21(DE3)/pETDuet-1-PPTGDHE3-GDH shows the same molecular mass as the target protein, and the brand in the first lane corresponding to the protein expressed by *E. coli* BL21(DE3)/pETDuet-1-PPTGDHE3 has the same migration distance as the protein expressed by *E. coli* BL21(DE3)/pET28b-GDH in the third lane, which means the recombinant strain *E. coli* BL21 (DE3)/pETDuet-1-PPTGDHE3-GDH expressed successfully.

2, Preparation of wet cells containing glufosinate-ammonium dehydrogenase E3-glucose dehydrogenase and crude enzyme solution thereof: the recombinant strain *E. coli* BL21(DE3)/pETDuet-1-PPTGDH E3-GDH containing the glucose dehydrogenase and the glufosinate-ammonium dehydrogenase E3 was inoculated into LB liquid medium containing 50 u g/mL ampicillin, incubated at 37° C. and 200 rpm for 12 h, the resulting inoculum was inoculated with 1% (v/v) incubating volume to fresh LB liquid medium containing 50 µg/mL ampicillin, incubated at 37° C. and 150 rpm until OD600=0.6–0.8 was achieved, added with IPTG at a final concentration of 24 µg/mL, incubated at 18° C. for 16 h, and centrifuged at 4° C. and 8000 rpm for 20 min, the supernatant was discarded, and the pellet was collected and washed twice with a pH 7.5, 20 mM phosphate buffer (PBS), thereby obtaining the wet cells.

The wet cells of the recombinant *E. coli* BL21(DE3)/pETDuet-1-PPTGDHE3-GDH were resuspended in pH 7.5, 100 mM PBS, and then subjected to ultrasonic disintegration in an ice-water mixture for 10 min. The conditions of the ultrasonic disintegration are 400 W, is on, and 5 s off, thereby obtaining a crude enzyme solution.

Example 5: Establishment of a Mutant Library of Glufosinate-Ammonium Dehydrogenase Genes 1. Site-directed saturation mutagenesis Take *E. coli* BL21 (DE3)/pETDuet-1-PPTGDHE3-GDH constructed in Example 2 as the starting strain.

The glufosinate-ammonium dehydrogenase mutant library was prepared by 4 rounds of site-directed saturation mutagenesis. The primers are shown in Table 2. In the first round, with the plasmid pETDuet-1-PPTGDHE3-GDH as a template and 107F and 107R shown in Table 2 as primers, saturation mutation PCR was carried out to mutate leucine at position 107 of the amino acid sequence of the glufosinate-ammonium dehydrogenase E3 shown in SEQ ID No. 6 into other 12 amino acids, the first PCR product was subjected to transformation and spreading, and the superior strain was selected, thereby obtaining a glufosinate-ammonium dehydrogenase mutant pETDuet-1-PPTGDHE3-GDH-L107R. In the second round, with the mutant pETDuet-1-PPTGDH E3-GDH-L107R as a template and 188F and 188R shown in Table 2 as primers, saturation mutation PCR was carried out, the second PCR product was subjected to transformation and spreading, and the superior strain was selected, thereby obtaining a glufosinate-ammonium dehydrogenase mutant pETDuet-1-PPTGDHE3-GDH-L107R-F188P. In the third round, with the mutant pETDuet-1-PPTGDHE3-GDH-L107R-F188P as a template and 239F and 239R shown in Table 2 as primers, saturation mutation PCR was carried out, the third PCR product was subjected to transformation and spreading, and the superior strain was selected, thereby obtaining a glufosinate-ammonium dehydrogenase mutant pETDuet-1-PPTGDHE3-GDH-L107R-F188P-G239K. In the fourth round, with the mutant pETDuet-1-PPTGDHE3-GDH-L107R-F188P-G239K as a template and 357F and 357R shown in Table 2 as primers, saturation mutation PCR was carried out, the fourth PCR product was subjected to transformation and spreading, and the superior strain was selected, thereby obtaining a glufosinate-ammonium dehydrogenase mutant pETDuet-1-PPTGDH E3-GDH-L107R-F188P-G239K-F357G.

The mutation PCR system (100 µL) was as follows: 2×Phanta Max buffer 25 µL, dNTPs 1 µL, forward and reverse primers 1 µL respectively, template 1 µL, Pfu DNA DNA polymerase 0.5 µL, and ddH$_2$O to a final volume of 50 µL. The conditions of the PCR procedure were as follows: pre-denaturation at 95° C. for 3 min; followed by 30 cycles of 95° C. for 15 s, 60° C. for 15 s and 72° C. for 7 min 20 s, and a final extension step at 72° C. for 10 min. The PCR result was checked by DNA agarose gel electrophoresis. The PCR product was treated with DpnI at 37° C. and 200 rpm for 1 h to digest the template, the DpnI was inactivated at 65° C. for 1 min, the resulting plasmid was introduced into *E. coli* BL21(DE3) by heat shock method, the bacteria solution was subjected to recovery at 37° C. and 200 rpm for 1 h, then was spread onto an LB plate containing 50 µg/mL ampicillin, and invertedly incubated overnight at 37° C., the superior mutants were selected from the obtained mutants and sent to Hangzhou Qingke Biotechnology Co., Ltd. for sequencing and stored.

TABLE 2

Design of primers for site-directed saturation mutation of glufosinate-ammonium dehydrogenase

| Primers | Primer sequence (5'-3') |
| --- | --- |
| 107 | F: GTCTTAAAATTCNDTGCGTTCGAGCAA<br>R: TTGCTCGAACGCAHNGAATTTTAAGAC |
| 188 | F: CTGTCTAACCAGNDTACCTCGGTACTTA<br>R: TAAGTACCGAGGTAHNCTGGTTAGACAG |
| 239 | F: CATTAGTGGCTCTNDTAACGTAGCGCAGT<br>R: ACTGCGCTACGTTAHNAGAGCCACTAATG |
| 357 | F: GCGGTTGATCTGNDTATCGAAGCGGGTA<br>R: TACCCGCTTCGATAHNCAGATCAACCGC |

Example 6: High-Throughput Screening of Gene Mutant Libraries

I. Establishment of a High-Throughput Screening Method for Glufosinate-Ammonium Dehydrogenase Prepare 50 mL of working solution as follows: 0.013 g of o-phthalaldehyde, 0.032 g of N-acetyl-L-cysteine and a pH9.8 boric acid buffer to a final volume of 50 mL as a working solution for high-throughput screening. Prepare 50 μL of 1 mM racemic glufosinate-ammonium using a pH9.8 boric acid buffer, react it with 50 μL of the working solution for 30 s with shaking, then add 100 μL of ddH$_2$O.

II. High-Throughput Screening

The mutant library obtained in Example 5 was introduced into E. coli BL21(DE3) competent cells, and the transformation conditions were as follows: add the PCR product to the competent cells, keep in an ice bath for 30 min, carry out heat shock at 42° C. for 90 s, pick single colonies on the LB plate containing 50 μg/mL ampicillin, use a sterilized toothpick to pick the single colonies into a sterilized 96-well deep well plate with 1 mL of LB medium containing 50 μg/mL ampicillin each well, cultivate on a shaker at 37° C. and 200 rpm for 8 hours, aspirate 500 μL of the bacterial solution from each well and transfer to another 96-well deep well plate with 500 μL of LB medium containing ampicillin and 24 μg/mL (final concentration) IPTG each well, place on a shaker at 18° C. and 200 rpm for 16 hours, centrifuge, collect the cells at the bottom of the 96-well deep well plate, thereby obtaining wet cells of 4576 recombinant E. coli strains containing a mutant gene.

1. Preliminary screening:

Preparation of a reaction solution: add PPO (2-carbonyl-4-[(hydroxy)(methyl)phosphinoyl]-butyric acid) at a final concentration of 10 mM, inorganic amino donor (NH$_4$)$_2$SO$_4$ at a final concentration of 50 mM and glucose at a final concentration of 12 mM in a pH7.5 phosphate buffer as a reaction medium to construct a reaction solution. Add 500 μL of the reaction solution in each well of the 96-well deep well plate while repeatedly pipetting with a pipette to resuspend the cells collected in the 96-well deep well plate, place the 96-well deep well plate on a shaker at 35° C. and 200 rpm for 4 hours, take the supernatant by centrifugation and measure the fluorescence value at λex=340 nm and λem=455 nm, and screen the strains with higher fluorescence value than the original strain.

2. Re-screening:

The crude enzyme solution of the strain obtained by the preliminary screening was used as a catalyst, 2-carbonyl-4-[(hydroxy)(methyl)phosphinoyl]-butyric acid was used as a substrate, glucose was used as an auxiliary substrate, and NADPH in vivo was used rather than exogenous NADPH or NADP+, thereby constructing a coenzyme circulation system. The reaction system was 10 mL, the amount of the catalyst calculated by the total amount of the wet cells was 50 g/L before ultrasonic disintegration, the final concentration of substrate was 300 mM, and the final concentration of glucose was 450 mM, the final concentration of inorganic amino donor (NH$_4$)$_2$SO$_4$ was 1M, after the reaction was carried out at 30° C. and 600 rpm for 10 min, 100 μL of the reacting solution was sampled and added with 5 μL of hydrochloric acid to terminate the reaction, and then added with ultrapure water to a final volume of 1 mL, that was, the reaction solution was diluted 10-fold, the diluted reaction solution was first subjected to derivatization treatment, 200 to 1 of the diluted reacting solution added with 400 μL of a derivatization reagent were subjected to derivatization at 30° C. for 5 min, 400 μL of ultrapure water was added to a final volume of 1 mL, the resulting mixture was centrifuged at 12000 rpm for 1 min, the supernatant was passed through a 0.22 μm membrane filter, and the filtrate was taken as a liquid sample to detect 2-carbonyl-4-[(hydroxy)(methyl) phosphinoyl]-butyric acid, L-glufosinate-ammonium, D-glufosinate-ammonium and ee value by HPLC. Using the product L-glufosinate-ammonium and the ee value as indicators, the superior mutants were screened, and the experimental results are shown in Table 3.

TABLE 3

Catalytic performance and stereoselectivity of PPTGDH and its mutants

| Strains | L-glufosinate-ammonium (mM)$^a$ | ee(%) |
|---|---|---|
| PPTGDH | 49.7 ± 0.5 | 99.5 |
| PPTGDH-L107Y | 99.2 ± 0.8 | 99.5 |
| PPTGDH-L107R | 217.8 ± 0.6 | 99.5 |
| PPTGDH-L107S | 28.3 ± 2.5 | 99.5 |
| PPTGDH-L107H | 39.2 ± 0.9 | 99.5 |
| PPTGDH- L107R-F188V | 25.7 ± 1.5 | 99.5 |
| PPTGDH- L107R-F188P | 250.8 ± 0.9 | 99.5 |
| PPTGDH- L107R-F188H | 36.0 ± 0.4 | 99.5 |
| PPTGDH- L107R-F188S | 35.2 ± 2.1 | 99.5 |
| PPTGDH- L107R-F188H | 40.2 ± 0.2 | 99.5 |
| PPTGDH- L107R-F188Y | 202.6 ± 1.8 | 99.5 |
| PPTGDH- L107R-F188G | 41.8 ± 2.0 | 99.5 |
| PPTGDH- L107R-G239V | 152.6 ± 0.2 | 99.5 |
| PPTGDH- L107R-G239K | 260.4 ± 1.5 | 99.5 |
| PPTGDH- L107R-G239D | 88.4 ± 0.3 | 99.5 |
| PPTGDH- L107R-G239I | 45.5 ± 0.9 | 99.5 |
| PPTGDH- L107R- G239K | 49.6 ± 0.2 | 99.5 |
| PPTGDH- L107R-G239D | 39.6 ± 1.5 | 99.5 |
| PPTGDH- L107R-G239H | 51.0 ± 0.8 | 99.5 |
| PPTGDH- L107R-G239S | 75.5 ± 0.3 | 99.5 |
| PPTGDH- L107R-F188P-G239Y | 252.7 ± 1.3 | 99.5 |
| PPTGDH- L107R-F188P-G239C | 270.2 ± 2.0 | 99.5 |
| PPTGDH- L107R-F188P-G239K | 283.2 ± 0.8 | 99.5 |
| PPTGDH-L107R-F188P-G239K-F357 G | 292.4 ± 2.2 | 99.5 |

It is shown in Table 3 that the production of L-glufosinate-ammonium of the mutants PPTGDH-L107R, PPTGDH-L107R-F188P, PPTGDH-L107R-G239K, PPTGDH-L107R-F188P-G239Y, PPTGDH-L107R-F188P-G239C, PPTGDH-L107R-F188P-G239K and PPTGDH-L107R-F188P-G239K-F357G is obviously higher than the original strain.

Example 7 Determination of Kinetic Parameters of the Original Glufosinate-Ammonium Dehydrogenase and Mutants Thereof 1. Purification of target proteins: the superior mutant strains (PPTGDH-L107R, PPTGDH-L107R-F188P, PPTGDH-L107R-G239K, PPTGDH-L107R-F188P-G239Y, PPTGDH-L107R-F188P-G239C, PPTGDH-L107R-F188P-G239K and PPTGDH-L107R-F188P-G239K-F357G) obtained in Example 6 and the original strain PPT-GDHE3 were used to obtain wet cells of the glufosinate-ammonium dehydrogenase mutants and the original enzyme according to the method in Example 2, the wet cells were respectively resuspended in buffer A (pH 8.0, 50 mM sodium phosphate buffer containing 0.3 M NaCl and 30 mM imidazole), subjected to ultrasonic disintegration for 20 min(ice bath, 400 W, 1 second on and 5 seconds off), and centrifuged at 4° C. and 12000 rpm for 20 min, then the supernatant was collected. The mutant proteins were purified by Ni-NTA column(1.6×10 cm, Bio-Rad, the USA), and the specific operations were carried out as follows: ①equilibrate a Ni-NTA column with 5 column volumes of a binding buffer(pH 8.0, 50 mM sodium phosphate buffer containing 0.3 M NaCl) until the baseline is steady; ②load the sample with a flow rate of 1 mL/min with the amount of the loading sample of 25-40 mg/mL, thereby attaching the target protein to the Ni-NTA column; ③wash the column with 6 column volumes of buffer A (pH 8.0, 50 mM sodium phosphate buffer containing 0.3 M NaCl and 30 mM imidazole) at a flow rate of 1 mL/min until the baseline is steady; ④wash the column with buffer B (pH 8.0, 50 mM sodium phosphate buffer containing 0.3 M NaCl and 500 mM imidazole) at a flow rate of 1 mL/min, collect the target protein and dialyze overnight in a pH 7.5, 20 mM phosphate buffer, thereby obtaining the pure glufosinate-ammonium dehydrogenase; and ⑤wash the Ni-NTA column with 5 column volumes of a binding buffer(pH 8.0, 50 mM sodium phosphate buffer containing 0.3 M NaCl) until the baseline is steady, and store the Ni-NTA column in 5 column volumes of ultrapure water containing 20% ethanol.

2. Kinetic parameters of the amino acid hydrogenase and its mutants were examined: 2-carbonyl-4-[(hydroxy)(methyl)phosphinoyl]-butyric acid was taken as substrate, the concentration was set as 2-10 mM(2, 4, 6, 8, 10 mM), the concentration of the exogenous coenzyme NADPH was set as 1-5 mM(1, 2, 3, 4, 5 mM), the final concentration of inorganic amino donor $(NH_4)_2SO_4$ was 10-50 mM, and a certain amount of a pure enzyme solution of the original glufosinate-ammonium dehydrogenase E3 strain and its mutants PPTGDH-L107R, PPTGDH-L107R-F188P, PPTGDH-L107R-G239K, PPTGDH-L107R-F188P-G239Y, PPTGDH-L107R-F188P-G239C, PPTGDH-L107R-F188P-G239K and PPTGDH-L107R-F188P-G239K-F357G.

The reaction system was 500 μL, the collected pure enzyme solution was diluted 10-fold with a pH 7.5, 100 mM phosphate buffer, 100 μL of the diluted solution was taken and added with the substrate, exogenous coenzyme NADPH and inorganic amino donor $(NH_4)_2SO_4$, a pH 7.4, 100 mM phosphate buffer was taken as a reaction medium, after reacting at 35° C. and 600 rpm for 10 min, the reaction solution was sampled to detect the concentration of L-glufosinate-ammonium using HPLC.

According to sequential mechanism in glufosinate-ammonium dehydrogenase's catalytic reaction, $v_{max}$, $K_m^A$, $K_m^B$ can be calculated by a double-reciprocal plot, the results were shown in Table 4. Comparing $k_{cat}$ and $K_m$, it can be found that the mutants PPTGDH-F357G and PPTGDH-L107R-F188P had an increase while the rest of the mutants had a certain decrease which meant an increase of affinity with 2-carbonyl-4-[(hydroxy methyl)phosphinoyl]-butyric acid and NADPH.

Catalytic efficiency $k_{cat}/k_m^B$ of the mutant PPTGDH-L107R-F188P-G239K-F357G (the amino acid sequence is shown in SEQ ID NO. 9) for 2-carbonyl-4-[(hydroxy)(methyl)phosphinoyl]-butyric acid reached 337.73 $s^{-1} \cdot mM^{-1}$, which was 22.19 times higher than that of the original enzyme (kcat/Km=15.22 $s^{-1} \cdot mM^{-1}$), and catalytic efficiency for the coenzyme NADPH reached 13703 $s^{-1} \cdot mM^{-1}$, which was 34.61 times higher than that of the original enzyme(kcat/Km=395.91 $s^{-1} \cdot mM^{-1}$) (Table 4).

Figure 5:
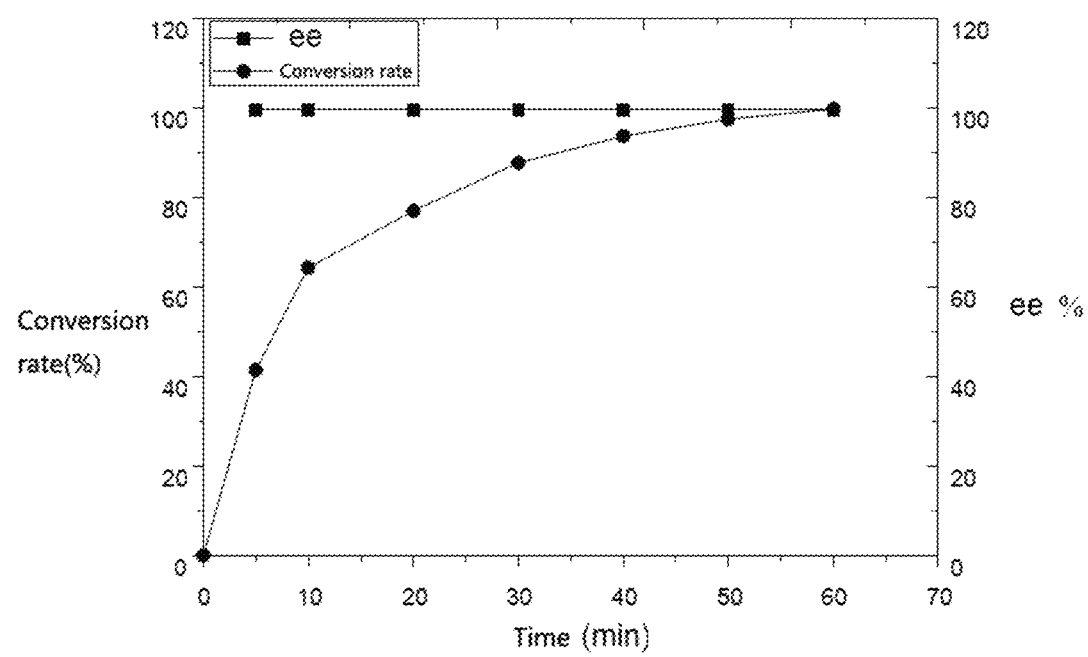
FIG. 5 is a reaction progress diagram of *E. coli* BL21 (DE3)/pETDuet-1-PPTGDHE3-L107R-F188P-G239K-F357G.

Example 8: Glufosinate-Ammonium Dehydrogenase Mutant E. coli BL21(DE3)/pETDuet-1-PPTGDHE3-GDH-L107R-F188P-G239K-F357G Catalyzes Asymmetric Reductive Amination of 2-Carbonyl-4-[(Hydroxy)(Methyl)Phosphinoyl]-Butyric Acid to Produce L-Glufosinate-Ammonium According to the method in Example 4, 0.75 g of wet cells of the glufosinate-ammonium dehydrogenase mutant strain E. coli BL21(DE3)/pETDuet-1-PPTGDHE3-GDH-L107R-F188P-G239K-F357G were obtained by fermentation, then the wet cells were added with 2-carbonyl-4-(hydroxymethylphosphinyl)-butyric acid at a final concentration of 500 mM, glucose at a final concentration of 750 mM and inorganic amino donor $(NH_4)_2SO_4$ at a final concentration of 1.5M, thereby constructing a reaction system with a volume of 30 ml, the reaction was carried out in a magnetic stirrer at 35° C. and 500 rpm for 1 h, ammonia water was flow-added to maintain the pH of the reaction solution at 7.5. The liquid phase method was used to detect the product L-glufosinate-ammonium and change of the e.e. value during the reaction, and the reaction processing curve was shown in FIG. 5. The figure showed that the concentration of the product was gradually increased with time, the reaction was completed within 40 minutes, the substrate conversion rate was greater than 99%, and the product e.e. value was always greater than 99.5%.

It can be seen from the above experimental results that the recombinant E. coli containing the glufosinate-ammonium dehydrogenase gene obtained in the present invention have a strong catalytic ability and can use 2-carbonyl-4-[(hydroxy)(methyl)phosphinoyl]-butyric acid as a substrate for biological conversion reaction to prepare a highly optically pure pesticide-L-glufosinate-ammonium.

TABLE 4

Comparison of kinetic parameters of the original strain PPTGDH and its mutants

| Enzyme | $k_{cat}$ $(s^{-1})^a$ | $K_m^A$ $(mM)^b$ | $K_m^B$ $(mM)^b$ | $k_{cat}/K_m^A$ $(s^{-1} \cdot mM^{-1})$ | $k_{cat}/K_m^B$ $(s^{-1} \cdot mM^{-1})$ |
|---|---|---|---|---|---|
| PPTGDH | 47.51 ± 2.05 | 0.12 | 3.12 | 3107.91 | 15.22 |
| PPTGDH-L107R | 42.02 ± 2.47 | 0.102 | 2.43 | 411.96 | 17.29 |
| PPTGDH-F188P | 33.50 ± 1.51 | 0.14 | 4.16 | 239.29 | 8.05 |
| PPTGDH-G239K | 33.98 ± 1.55 | 0.068 | 2.53 | 499.70 | 13.43 |
| PPTGDH-F357G | 56.31 ± 1.80 | 0.105 | 3.35 | 536 | 16.808 |
| PPTGDH-L107R-F188P | 67.10 ± 2.81 | 0.112 | 3.22 | 599.11 | 20.84 |
| PPTGDH-L107R-F188P- G239K | 607.5 ± 4.02 | 0.045 | 2.09 | 13500 | 290.67 |
| PPTGDH-L107R-F188P-G239K-F357G | 712.6 ± 3.21 | 0.052 | 2.11 | 13703 | 337.73 |

The invention claimed is:

1. A method for the production of L-glufosinate ammonium comprising contacting a variant of the polypeptide of SEQ ID NO: 6 having glufosinate-ammonium dehydrogenase activity with 2-carbonyl-4-[(hydroxy)(methyl)phosphinoyl]-butyric acid, wherein said variant comprises all of SEQ ID NO: 6 except for (i) a substitution that corresponds to the substitution L107R in the polypeptide of SEQ ID NO: 6, and (ii) one or more substitutions that correspond to the substitutions in the polypeptide of SEQ ID NO: 6 selected from the group consisting of F188P, G239K, G239Y, G239C and F357G.

2. The method of claim 1, wherein said variant is in a catalyst, wherein said catalyst is in the form of wet cells that comprise said variant or a crude enzyme solution that comprises said variant, wherein said method comprises:
   (a) adding said catalyst, 2-carbonyl-4-[(hydroxy)(methyl)phosphinoyl]-butyric acid, glucose and an inorganic amino donor to a pH 7.5 buffer to form a reaction solution;
   (b) maintaining the reaction solution at 35° C. and 600 rpm for the conversion of 2-carbonyl-4-[(hydroxy)(methyl)phosphinoyl]-butyric acid into L-glufosinate ammonium; and
   (c) subjecting the reaction solution to separation and purification to obtain L-glufosinate ammonium;
   wherein the wet cells are obtained by culturing a recombinant engineered strain comprising a gene encoding the variant and a gene encoding a glucose dehydrogenase, and wherein the crude enzyme solution is obtained by subjecting the wet cells to ultrasonic disintegration.

3. The method of claim 2, wherein the reaction solution (a) comprises 20 g/L to 100 g/L of wet cells, (b) has an initial concentration of 2-carbonyl-4-[(hydroxy)(methyl)phosphinoyl]-butyric acid from 10 mM to 500 mM, (c) has a glucose concentration from 12 mM to 600 mM, and (d) has an inorganic amino donor concentration from 50 mM to 1.5 M.

4. The method of claim 2, wherein the catalyst is prepared by:
   (a) inoculating LB medium containing 50 μg/mL ampicillin with a recombinant engineered strain comprising a gene encoding the variant and a gene encoding a glucose dehydrogenase, and incubating the LB medium at 37° C. and 200 rpm for 12 hours to obtain an inoculum;
   (b) inoculating fresh LB medium containing 50 μg/mL ampicillin with 1% by volume of the inoculum of (a), and incubating at 37° C. and 150 rpm to obtain a culture;
   (c) adding IPTG to the culture of (b) when OD600 reaches 0.6-0.8 and culturing for 16 hours;
   (d) centrifuging the culture of (c) at 4° C. and 8000 rpm for 20 minutes and discarding the supernatant;
   (e) collecting the pellet obtained from step (d) and washing the pellet with a pH 7.5, 20 mM phosphate buffer to obtain wet cells; and
   (f) resuspending the wet cells of (e) with a pH 7.5, 100 mM PBS buffer and subjecting the wet cells to ultrasonic disintegration in an ice-water mixture for 10 minutes to obtain a crude enzyme solution, wherein the conditions of the ultrasonic disintegration are 400 W and 1 second on and 5 seconds off.

5. The method of claim 2, wherein the variant comprises all of SEQ ID NO: 6 except for substitutions that corresponds to substitutions L107R, F188P, G239K and F357G in the polypeptide of SEQ ID NO: 6.

* * * * *